US010266737B2

(12) United States Patent
Van Horn et al.

(10) Patent No.: US 10,266,737 B2
(45) Date of Patent: Apr. 23, 2019

(54) ADSORPTION SYSTEMS USING METAL-ORGANIC FRAMEWORKS

(71) Applicants: Arkema Inc., King of Prussia, PA (US); Battelle Memorial Institute, Richland, WA (US)

(72) Inventors: Brett L. Van Horn, King of Prussia, PA (US); Christopher A. Bertelo, Doylestown, PA (US); Gary S. Silverman, Lancaster, VA (US); B. Peter McGrail, Pasco, WA (US); Praveen K. Thallapally, Richland, WA (US); Radha K. Motkuri, Richland, WA (US); Jeromy J. Jenks, Benton City, WA (US)

(73) Assignee: Arkema Inc., King of Prussia, PA (US)

( * ) Notice: Subject to any disclaimer, the term of this patent is extended or adjusted under 35 U.S.C. 154(b) by 57 days.

(21) Appl. No.: 14/420,042

(22) PCT Filed: Aug. 14, 2013

(86) PCT No.: PCT/US2013/054863
§ 371 (c)(1),
(2) Date: Feb. 6, 2015

(87) PCT Pub. No.: WO2014/028574
PCT Pub. Date: Feb. 20, 2014

(65) Prior Publication Data
US 2015/0291870 A1 Oct. 15, 2015

Related U.S. Application Data

(60) Provisional application No. 61/683,322, filed on Aug. 15, 2012.

(51) Int. Cl.
| | | |
|---|---|---|
| *C09K 5/14* | (2006.01) | |
| *C09K 5/04* | (2006.01) | |
| *C07F 11/00* | (2006.01) | |
| *C07F 15/02* | (2006.01) | |
| *C07F 15/04* | (2006.01) | |
| *C07F 15/06* | (2006.01) | |
| *C07F 19/00* | (2006.01) | |
| *C07F 1/00* | (2006.01) | |
| *C07F 3/00* | (2006.01) | |
| *B01D 53/02* | (2006.01) | |
| *C01C 3/11* | (2006.01) | |
| *C07C 63/28* | (2006.01) | |
| *C07C 63/307* | (2006.01) | |
| *C07C 65/03* | (2006.01) | |
| *F25B 15/00* | (2006.01) | |
| *B01J 20/22* | (2006.01) | |

(52) U.S. Cl.
CPC .............. *C09K 5/047* (2013.01); *B01D 53/02* (2013.01); *B01J 20/226* (2013.01); *C01C 3/11* (2013.01); *C07C 63/28* (2013.01); *C07C 63/307* (2013.01); *C07C 65/03* (2013.01); *C07F 1/005* (2013.01); *C07F 3/003* (2013.01); *C07F 11/005* (2013.01); *C07F 15/025* (2013.01); *C07F 15/045* (2013.01); *C07F 15/065* (2013.01); *C07F 19/005* (2013.01); *C09K 5/14* (2013.01); *F25B 15/006* (2013.01); *B01D 2253/204* (2013.01); *F25B 2315/006* (2013.01)

(58) Field of Classification Search
CPC .......... C09K 5/047; C09K 5/14; B01D 53/02; C01C 3/11; C07C 63/28; C07C 63/307; C07C 65/03; C07F 1/005; C07F 11/005; C07F 15/025; C07F 15/045; C07F 15/065; C07F 19/005; C07F 3/003; F25B 15/006
USPC ............. 252/69; 423/371; 556/113, 147, 61; 562/476; 62/476; 95/90
See application file for complete search history.

(56) References Cited

U.S. PATENT DOCUMENTS

| | | | |
|---|---|---|---|
| 6,736,991 B1 | 5/2004 | Cohen et al. | |
| 7,847,115 B2 | 12/2010 | Schubert et al. | |
| 8,227,375 B2 | 7/2012 | Willis et al. | |
| 2004/0069144 A1 | 4/2004 | Wegeng et al. | |
| 2009/0263621 A1* | 10/2009 | Chang | B01D 53/28 428/116 |
| 2009/0272134 A1 | 11/2009 | Hulse et al. | |
| 2010/0132359 A1 | 6/2010 | Minhas et al. | |
| 2010/0229587 A1 | 9/2010 | Liu et al. | |
| 2011/0226004 A1* | 9/2011 | Kontomaris | C09K 5/047 62/476 |
| 2011/0232305 A1 | 9/2011 | Minhas et al. | |

(Continued)

FOREIGN PATENT DOCUMENTS

| | | |
|---|---|---|
| EP | 2 230 288 A2 | 3/2010 |
| WO | WO 97/14762 | 4/1997 |
| WO | WO 2014/028574 A2 | 2/2014 |

OTHER PUBLICATIONS

Felix Jeremias et al., "MIL-100(Al, Fe) as water adsorbents for heat transformation purposes—a promising application", Journal of Materials Chemistry, 2012, 22, 10148-10151 (published on-line Dec. 23, 2011).*

(Continued)

*Primary Examiner* — Douglas J McGinty
(74) *Attorney, Agent, or Firm* — Steven D. Boyd

(57) ABSTRACT

The present invention relates to sorbants such as metal-organic frameworks (MOFs), covalent organic frameworks (COFs), porous aromatic frameworks (PAFs) or porous polymer networks (PPNs) for separations of gases or liquids, gas storage, cooling, and heating applications, including, but not limited to, adsorption chillers.

11 Claims, 14 Drawing Sheets

(56) References Cited

U.S. PATENT DOCUMENTS

| | | |
|---|---|---|
| 2011/0243820 A1 | 10/2011 | McGrail et al. |
| 2011/0284181 A1 | 11/2011 | Rached |
| 2012/0118153 A1 | 5/2012 | Omary et al. |
| 2012/0172612 A1 | 7/2012 | Yaghi et al. |
| 2012/0304686 A1* | 12/2012 | Kontomaris .......... F25B 15/008 62/478 |
| 2013/0283849 A1 | 10/2013 | Baumann et al. |
| 2015/0238930 A1* | 8/2015 | Said ...................... B01J 20/226 502/401 |

OTHER PUBLICATIONS

Concise Science Dictionary, "earth's atmosphere", Oxford University Press, 1984, pp. 218-219.*

* cited by examiner

ADSORPTION SYSTEMS USING METAL-ORGANIC FRAMEWORKS

This present application is the national phase under 35 USC § 371 of prior PCT International Application Number PCT/US2013/054863 filed Aug. 14, 2013 which designated the United States of America and claimed priority to U.S. Provisional Patent Application Ser. No. 61/683,322 filed Aug. 15, 2012.

SUMMARY OF INVENTION

The present invention relates to sorbants such as metal-organic frameworks (MOFs), covalent organic frameworks (COFs), porous aromatic frameworks (PAFs) or porous polymer networks (PPNs) for separations of gases or liquids, gas storage, cooling, and heating applications, such as, but not limited to, adsorption chillers.

BACKGROUND OF INVENTION

Adsorption cooling technology is an established alternative to mechanical vapor compression refrigeration systems. Adsorption-based refrigeration systems have several advantages including few moving parts, reduced vibration and lubrication requirements, and scalability to refrigeration load from a few watts to several kilowatts. Key disadvantages include large thermal mass, bulkiness, complex controls, and low COP (0.2 to 0.6). These disadvantages arise mostly from thermophysical property limitations of adsorbent-refrigerant combinations presently available.

In the United States, various types of chiller technologies deployed in commercial buildings consume approximately 0.6 quads annually. Adsorption chillers, while currently a relatively small percentage of the chiller market, represent an important alternative to mechanical vapor compression refrigeration systems. Adsorption chillers use low-grade heat to drive a thermal compressor. Low-grade industrial heat sources range from waste heat produced in manufacturing to solar thermal installations. Adsorption-based cooling systems have several advantages: using low-grade heat sources; include few moving parts; reduced vibration and lubrication requirements; and scalability of cooling load from a few watts to several kilowatts. Key disadvantages of a typical adsorption chiller system include large thermal mass, bulkiness, and low COP (0.2 to 0.6). The low COP is the most significant factor that drives up the size and cost of the units per ton of cooling capacity delivered and thus is a significant barrier to more widespread use of this technology.

A basic adsorption chiller machine consist of two sorbent chambers, one evaporator, and one condenser. While the sorbent in the first compartment (desorber) is regenerated using heat from the external heat source, such as from hot water, the sorbent in the second compartment (adsorber) adsorbs the vapor of the working fluid entering from the evaporator; this compartment has to be cooled in order to enable a continuous adsorption. The working fluid is evaporated in the evaporator, and through heat exchange is used to cool or chill an external heat transfer fluid, typically water (e.g. chilled water). When the sorbent in the adsorber becomes saturated with working fluid, the function of the compartments is switched. Exemplary, non-limiting, schematics of basic adsorption chiller systems are shown in FIGS. 1 and 2. In a basic configuration, a hot fluid, such as hot water, is used to heat the desorber to regenerate the sorbent; a cool fluid, such as cool water, is used to cool the sorbent in the adsorber; a cool fluid is used to cool the condenser, optionally being the same fluid or fluid stream as used to cool the adsorber; chilled fluid, such as chilled water is cooled in the evaporator. Various configurations of heat exchangers or heat transfer configurations can be used in the evaporator, condenser, adsorber, and desorber. Various control and engineering schemes may be used to switch the functions of the two sorbent chambers. In a non-limiting example, the connection between the sorbent chambers and the evaporator and condenser may include flapper values; when chamber 1 is the desorber and chamber 2 is the adsorber (as in FIGS. 1 and 2) the flapper valve(s) connecting chamber 1 to the evaporator is(are) closed while the flapper valve(s) connecting champer 1 to the condenser is(are) open; and the flapper valve(s) connecting chamber 2 to the evaporator is(are) open while the flapper valve(s) connecting champer 2 to the condenser is(are) closed; when switching the functions of the two sorbent chambers the open/closed positions of the flappers values are switched. In a non-limiting example, when the functions of the two sorbent chambers are switched the circuits for the hot fluid and cool fluid may also be switched, such as through the use of controlled valves. The system may also consist of a circuit to return liquid working fluid condensed in the condenser back to the evapor.

The present invention is directed toward adsorption systems having very high mass loading and relatively low heats of adsorption comprising certain combinations of refrigerants and sorbents such as metal-organic framework (MOF) which provide highly efficient adsorption chillers.

DETAILED DESCRIPTION OF INVENTION

Figure 1:
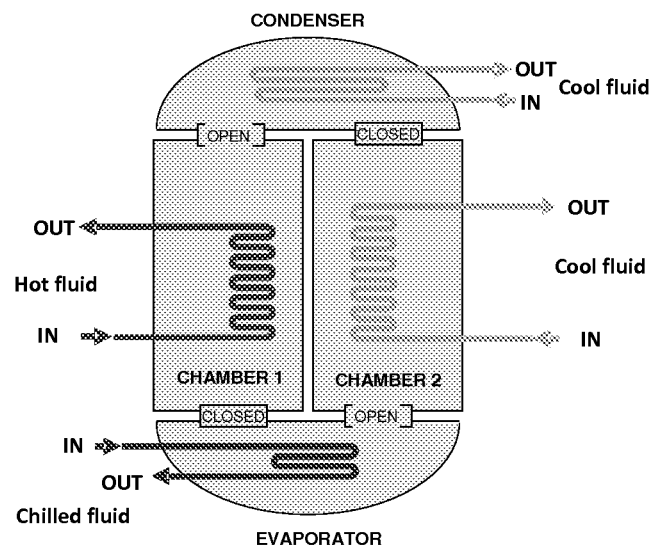
FIG. 1 is a schematic of an adsorption chiller system.
Figure 2:
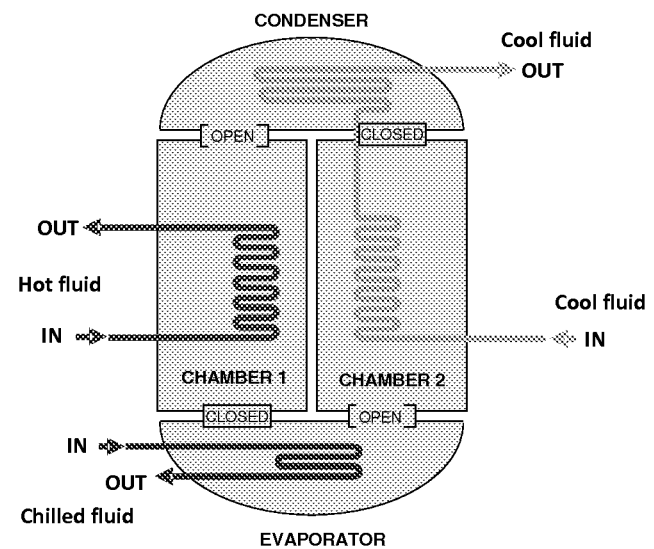
FIG. 2 is a schematic of an adsorption chiller system.

The present invention relates to sorbants such as metal-organic frameworks (MOFs), covalent organic frameworks (COFs), porous aromatic frameworks (PAFs) or porous polymer networks (PPNs) for separations of gases or liquids, for gas storage, and for cooling and heating applications. The present invention further relates to combinations of MOFs and certain working fluids for heat transfer operations. The present invention further relates to a double effect chiller system. MOFs are compounds consisting of metal ions or clusters coordinated to organic molecules, often rigid, to form one-, two-, or three-dimensional structures that can be porous. In some cases, the pores are stable to elimination of the guest molecules (often solvents) and can be used for the storage of gases such as hydrogen and carbon dioxide. Other possible applications of MOFs are in gas purification, in gas separation, in catalysis and as sensors.
Metal-Organic-Frameworks (MOFs)

In a preferred embodiment of the present invention, the metal-organic frameworks (MOFs) are porous metal organic frameworks or hybrid organic inorganic materials that include at least one metal component selected from the group consisting of Zn, Fe, Al, Mg, V, Ni, Mn, Co, Sc, Y, Ti, Zr, Hf, Nb, Ta, Cr, Mo, W, Tc, Re, Ru, Os, Ir, Pd, Pt, Cu, Ag, Au, Hg, Sr, Ba, Ga, In, Tl, Si, Ge, Sn, Pb, Sb, Bi, and combinations thereof.

In another preferred embodiment of the present invention, divalent metal ions including $Ni^{+2}$, $Zn^{+2}$, $Cu^{+2}$, $Co^{+2}$, $Mg^{+2}$, $Ca^{+2}$, $Fe^{+2}$, $Mn^{+2}$, and the like, and trivalent metal ions such as $Fe^{+3}$, $Al^{+3}$, $Cr^{+3}$, $Mn^{+3}$, and the like, are incorporated in the metal organic frameworks. In another embodiment, the porous metal organic frameworks may be formed by coordination with tetravalent, pentavalent or hexavalent metal ions of Zr, Ti, Sn, V, W, Mo or Nb.

In another preferred embodiment of the present invention, along with univalent metals ions, mixed metals containing divalent, trivalent oxidation states are incorporated in metal organic frameworks also known as prussian blue analogues with chemical formula of $M^{+3}_3[M^{+2}(CN)_6]_2$ where $M^{+3}$ can be $Fe^{+3}$, $CO^{+3}$, $Mn^{+3}$ etc and $M^{+2}$ can be $Zn^{+2}$, $Ni^{+2}$, $Co^{+2}$, $Mn^{+2}$, $Cu^{+2}$ and the like, and mixtures thereof.

An organic building block in the porous metal organic framework materials is referred to as a linker or organic linker. In one embodiment, the organic linker has a functional group capable of coordination. Examples of functional groups that can be coordinated with these metal ions include but are not limited to, carbonic acid (—$CO_3H$), anionic form of carbonic acid (—$CO_3^-$), carboxyl anion group of carboxylic acid, amino group (—$NH_2$), imino group, hydroxyl group (—OH), amido group (—$CONH_2$), sulfonic acid group (—$SO_3H$), anionic form of sulfonic acid (—$SO_3$), cyanide (—CN), nitrosyl (—NO) pyridine, and so on . . . . For example, in one embodiment the chemical formula T[Fe(CN)$_5$NO] where T=Mn, Fe, Co, Ni, Cu, Zn, and Cd; also mixed compositions include $Co_{1-x}T_x$[Fe(CN)$_5$NO]; T=Mn, Fe, Ni, Zn, and Cd etc. also known as nitroprussides In another embodiment, mixed metals and organic linkers are incorporated in metal organic frameworks also known as Hoffman clathrates. For example, chemical formula M(L)[M(X)$_4$]n$H_2O$ where M=Ni, Cu, Co, Zn, Mn, Fe etc., L=pyrazine, 4,4'-bipyridine, 1,2-bis(4-pyridyl)ethane, dipyridylacetylene etc., X=CN, etc., The organic ligand may include compounds having at least two sites for coordination, for example, bi-, tri-, tetra-, penta-, hexadentate ligands. Non-limiting examples of these organic compounds may be a neutral linker such as pyrazene, dabco, piperazine, bypiridene, azobenzene and functionalized forms of these neutral ligands etc., anionic organic compounds including anions of carboxylic acid such as, terephthalate, naphthalenedicarboxylate, beneznetricarboxylate, beneznetetracarboxylate, beneznepentacarboxylate, beneznehexacarboxylate, dioxo-terephthalate, etc. Anions of aromatic and other linear carboxylic acid anions include formate, oxalate, malonate, succinate, glutamate etc., and nonaromatic carboxylate anions including 1,2-cyclohexanedicarboxylate, 1,3-cyclohexanedicarboxylate, 1,4-cyclohexanedicarboxylate and 1,3,5 cyclohexane tricarboxylate can be used to prepare the hybrid organic inorganic materials.

Other organic linkers including various heterocyclic materials including, furan, indole, pyridine-2,3-dicarboxylate, pyridine-2,6-dicarboxylic acid, pyridine-2,5-dicarboxylic acid and pyridine-3,5-dicarboxylicacid, and the like.

Other organic linkers to produce a sub-class of metal organic frameworks called zeolite imidazolate frameworks generated using imidazole, tetrazole, trizole, and functionalized with Cl, Br, I, F, $NH_2$, $NO_2$ and so on.

In another preferred embodiment, the organic ligand can be dihydroxyterephthalate and its derivatives. In a non-limiting example, dihydroxyterephthalate having, chloro, bromo, iodo, fluoro, cyano, sulphonato, amino, aldehyde, carbamide and so on. Similarly, organic building blocks can be functionalized with di-, tri-, tetra, -pentaterephthalate containing at least one or more functional groups such as nitro, amino, bromo, chloro, iodo, amino and so on.

In a preferred embodiment, porous metal organic framework materials having chemical formula $M_3X(H_2O)_2[C_6L_{4-y}Z'_y(CO_2)_3$ (M=Cu, Fe, Zn, Ni, Cr, Mn, V, Al, Mg, Ca, Ti; X=Cl, Br, I, F, or OH; Z or Z'=H, $NH_2$, Br, I, $NO_2$ 0<y<4) or a hydrate. Another embodiment of porous metal organic framework of chemical formula include $M_3X(H_2O)_2O[C_6Z_{3-y}Z'_y(CO_2)_3]_2$ (M=Cu, Fe, Zn, Ni, Cr, Mn, V, Al, Mg, Ca, Ti; X=Cl, Br, I, F, or OH; Z or Z'=H, $NH_2$, Br, I, $NO_2$ 0<y<4). Other molecular formulas represented as $M_3OX_{1-y}(OH)_y[C_6H_3$—$(CO_2)_3]_2$ (0<y<1; M=Cu, Fe, Mn, Cr, V, Al, Ti, Zr, or Mg, X=Cl, Br, I, F, $NO_2$, $NH_2$, CHO. $M_3X_{1-y}(OH)_y(H_2O)_2O[C_6H_4(Co_2)_2]_3$; (0<y<1; M=Cu, Zn, Al, Mg, Fe, Ge, Ru, Rh, Mn, Ni; X=Cl, Br, I, F, etc). Another chemical formula of porous metal organic frameworks with hydrate is represented as $M_3O(H_2O)_2X_{1-y}(OH)_y[C_6H_3$—$(CO_2)_3]_2 \cdot nH_2O$ (0<y<1; (M=Cu, Fe, Mn, Cr, V, Al, Ti, Zr, or Mg, X=Cl, Br, I, F, NO=, $NH_2$, CHO, 0.1<n<150) $M_3X_{1-y}(OH)_y(H_2O)_2O[C_6H_4(CO_2)_2]_3 \cdot nH_2O$ (M=Cu, Fe, Mn, Cr, V, Al, Ti, Zr, or Mg, X=Cl, Br, I, F, NO2, NH2, CHO, 0.1<n<150).

Apart from porous metal organic frameworks of the chemical formula above, simple porous organic solids such as calix(n)arene, tert-butylcalix(n)arene, thiacalix(n)arene, tert-butylthiacalix(n)arene and functionalized with Cl, Br, I, $NH_2$, $NO_2$, $SO_3H$, $SO_3$, pyridyl, $OCH_3$ etc. . . . where n=4, 5, 6, 7 and 8, hydroquinones, tris-o-phenylenedioxycyclotriphosphazene (TPP), cucur(n)biturils (CB) where n=5, 6 and 7 may also be used.

Chemical formula of the calix[4]arene ($C_{28}H_{24}O_4$), p-tert-butylcalix[4]arene $C_{44}H_{56}O_4$, p-tert-butylthiacalix[4]arene $C_{40}H_{48}O_4S_4$, CB[6] $C_{36}H_{36}N_{24}O_{12}$, CB[7] $C_{42}H_{42}N_{28}O_{14}$, tert-butylcalix[5]arene ($C_{55}H_{70}O_5$), calix [5]arene ($C_{35}H_{30}O_5$)

In another embodiment of the present invention, the sorbent comprises a covalent organic frameworks. Covalent organic frameworks (COFs) or porous aromatic frameworks (PAFs) or porous polymer networks (PPNs) are porous crystalline extended aromatic framework materials where the organic building blocks are linked by strong covalent bonds. The attractiveness behind these materials was exclusively use of light elements such as H, B, C, N and O which are known to form well established materials (ex: graphite, diamond, boron nitride etc) with strong covalent bonds. The fine tunability of the organic building block with various functional groups, extending the size, lead to the formation of lightweight functionalized micro/meso porous covalent frameworks with desired applications. In a preferred embodiment of the present invention are covalent organic framework type materials, including, but not limited to those generated by condensation of diboronic acid, hexahydroxytriphenylene, dicyanobenzene and its derivatives of chemical formula $C_9H_4BO_2$ and so on, and those generated from benzene-1,4-diboronic acid (BDBA), 2,3,6,7,10,11-hexahydroxyltriphenylene (HHTP), tetrakis(4-bromophenyl)methane, Tetrakis(4-ethynylphenyl)methane (TEPM), 1,3,5,7-Tetrakis(4-ethynylphenyl)adamantine (TEPA), 1,3, 5,7-Tetrakis(4-bromophenyl)adamantine (TBPA). In preferred embodiment of the present invention, the covalent organic framework (COF) is selected from COF-1, COF-2, and mixtures thereof.

The MOF in accordance with the present invention can comprise cyanide-bridged metal organic frameworks. The cyanide-bridged metal-organic-frameworks may be of the chemical the formula $M_3^{II}[M^{III}(CN)_6]2.nH2O$ ($M^{II}$, $M^{III}$=transition metals) and constructed from octahedral $M^{III}(CN)63$—complexes that are bridged into a simple cubic lattice by M2+ ions. Through appropriate choice of metal ions ($M^{II}$ and $M^{III}$), sorbents with different properties can be constructed. For example, in an embodiment of the present invention, $M^{III}$=Co and the divalent metal $M^{II}$=Mn, Cu and/or Ni, with the resulting MOF sorbents as $Mn_3^{II}[Co^{III}(CN)_6]_2.nH2O$ (MnCo); $Cu_3^{II}[Co^{III}(CN)_6]_2.nH2O$(CuCo); $Ni_3^{II}[Co^{III}(CN)_6]_2.nH2O$(NiCo); $Co_3^{II}[Co^{III}(CN)_6]_2nH2O$ (CoCo); and $Zn_3^{II}[Co^{III}(CN)_6]_2.nH2O$(ZnCo).

Exemplary, non-limiting MOFs of the present invention include CuBTC, MDODBC, FMOF-2CU, MIL-101(Cr), MIL-101-X (X=NO2, NH2, Br, SO3H), MIL-100(Fe), MOF-74(Ni), MOF-74(Fe), MOF-74(Co), MOF-74(Cu), MOF-74(Zn), MIL-100(Fe), MOF-74(Ni), MOF-74(Fe), MOF-74(Co), UMCM-1 (University of Michigan Crystalline Material-1; PCN-222, [Zn4O(BDC)(BTB)4/3]), CoCo, ZnCo, and LZnPYC1. Exemplary methods of preparing these MOFs are further described below:

CuBTC: (Copper benzene-1,3,5-tricarboxylate, Cu-BTC MOF, HKUST-1) 1,3,5-benzene tricarboxylic acid (H3BTC) and copper(II) nitrate trihydrate ($Cu(NO_3)_2.3H_2O$), were dissolved in 24 mL of 1:1 (w/w) mixture of water and ethanol, and stirred magnetically for 10 min. The resulting reactant mixture was loaded into a Teflon autoclave, sealed and placed in a furnace overnight at 100° C. The solid products were washed with waterethanol mixture to remove the unreacted BTC and dried overnight. The single crystal X-ray analysis of CuBTC shows the BTC ligand is coordinated with Cu(II) paddle-wheels linked into a three dimensional porous structure. The pores are ovoid and approximately 1.0 μm in diameter.

MDOBDC: (M=metal, DOBDC is linker): To a solid mixture of 2,5-dihydroxyterephthalic acid (DOBDC), a corresponding metal nitrate (M=Mg, Ni, Zn, or Co) was added to a 15:1:1 (v/v/v) mixture of DMF-ethanol-water (500 mL) in a pyrex glass screw cap jar, which was further contained in a PTFE jar with PTFE screw-cap. The suspension was mixed and ultrasonicated until the reaction mixture was homogeneous. The reaction solution was then placed in an oven at 125° C. After 20 hours, the sample was removed from the oven and allowed to cool to room temperature. The mother liquor was decanted from the yellow microcrystalline material and replaced with methanol (200 mL). The methanol was decanted and replenished four times over two days. The solvent was removed under vacuum at 250° C. over 10 hours to activate the material. Crystallographic measurements were performed on a single crystal and showed the DOBDC contains a three dimensional honeycomb-like network structure, with a large one-dimensional cylindrical channel having a diameter about 11 Å. The metal sites in the framework are unsaturated following the removal of solvent molecules.

FMOF-2Cu: was obtained by heating a water solution containing 2,20-bis(4-carboxyphenyl) hexafluoropropane (CPHFP) and copper nitrate hexahydrate in a 1:2 ratio at 125° C. for 72 h. Crystallographic measurements of the resulting crystals show that the flexible V-shaped organic building block is connected to two copper atoms to generate a porous framework filled with coordinated solvent molecules. FMOF-2Cu contains irregular-shaped micro channels, with alternating large cages and small entrances (or necks) that connect these cages.

MIL-101(Cr): (chromium(III) terephthalate): was made under basic conditions using tetramethylammonium hydroxide (TMAOH). 1 mmol of $H_2BDC$ (166 mg) was added to an alkali solution (TMAOH, 5 ml, 0.05 mol/L) and stirred at room temperature for 10 min. To this solution, 1 mmol of $Cr(NO_3)_3.9H_2O$ (400 mg) was added and maintained the pH of 6.0-6.5. The reaction mixture was stirred for 20 min and then transferred into a 23 ml PTFE-lined autoclave and heated for 24 h at a temperature of 180° C. After slowly cooling to room temperature, the green powder was collected by repeated centrifugation and thorough washing with distilled water and methanol. MIL-101(Cr) is also called FMOF-1 or MIL-101.

MIL-100(Fe): (iron (III) carboxylate): A solution containing Fe-powder (10 mmol, 555 g), 1,3,5-benzene tricarboxylic acid ($H_3BTC$) (6.5 mmol, 1.375 g), hydrofluoric acid (0.4 ml, nitric acid (0.76 ml) and deionized water (50 ml) was filled in a 125 ml PTFE-liner. The PTFE-liner was placed in an autoclave and heated to 150° C. within 12 h. After six days, the autoclave was cooled to room temperature within 24 h. The reaction mixture was filtered and the solid light-orange product was heated in water for 3 h at 80° C. The product was filtered and dried in air at room temperature. The MIL-100Fe has pore diameters of 25 and 29 Å as confirmed by the single crystal X-ray diffraction. MIL-100(Fe) is also called FMOF-2 or MIL-100.

CoCo and ZnCo: The cyanide-bridged metal organic frameworks was of chemical formula $M_3^{II}[M^{III}(CN)_6]_2 \cdot nH2O$ ($M^{II}$, $M^{III}$=transition metals) and were constructed from octahedral $M^{III}(CN)_6^{3-}$ complexes that were bridged into a simple cubic lattice by $M^{2+}$ ions. Through appropriate choice of metal ions ($M^{II}$ and $M^{III}$), sorbents with different properties can be constructed. Three variants were synthesized by choosing $M^{III}$=Co and varying the divalent metal $M^{II}$=Mn, Cu and Ni. The resulting sorbents were $Co_3^{II}[Co^{III}(CN)_6]_2 \cdot nH2O$(CoCo); and $Zn_3^{II}[Co^{III}(CN)_6]_2 \cdot nH_2O$ (ZnCo). The synthesis involved slow mixing of 0.1 M aqueous solution of $K_3[Co(CN_6)]_2$ and 0.18M aqueous solution of each metal nitrate/chloride solution under vigorous stirring, followed by aging for 24 h. Precipitated solids were filtered, washed with deionized water, and dried in air.

LZnPYC1: was synthesized using an amino acid derived organic building block and zinc chloride in a 1:1 ratio of water and methanol at 80° C. The crystal structures show a hexagonal porous network structure filled with water molecules.

The MOFs of the present invention can be based on ligands comprising partially and fully fluorinated linkers such as 4,4-(hexafluoroisopropylidene)bis(benzoic acid) (HFBBA); 3,5-bis(trifluoromethyl)-1,2,4-triazolate; 2,2-bis (4-carboxyphenyl) hexafluoropropane; 3-fluoro-isonicotinic acid.

The MOFs of the present invention can be produced from transition metals. In a preferred embodiment, the transition metals are selected from $Co^{+2}$, $Mn^{+2}$, and $Cu^{+2}$. The MOFs of the present invention can be selected from: [Cu(HFBBA) $(phen)_2].2(H_2HFBBA)(H_2O)(HCO_2)]$, which may be produced from $Cu(NO_3)_2 \cdot 3H_2O$; 1,10-Phenanthroline (phen) and HFBBA. $[Cu(HFBBA)_2(2,2'-Bipy)_2(H_2O)]$ which may be produced from $Cu(NO_3)_2 \cdot 3H2O$, 2,2'-Bipyridyl (Bipy). $[Cu(HFBBA)(4,4'dime-2,2'-Bipy)(HCO_2)] \cdot (HFBBA)$ (H2O)] which may be produced from $Cu(NO_3)_2 \cdot 3H2O$; Bipy; and HFBBA. $[Cu_2(HFBBA)_2(3-mepy)_2] \cdot (DMF)_2(3-mepy)]$, which may be produced from $Cu(NO_3)_2 \cdot 3H_2O$; HFBBA; N,N-dimethylformamide (DMF), and 3-methylpyridine (3-mepy). [Cu(HFBBA) (Phen)] which may be produced from $Cu(NO_3)_2 \cdot 3H_2O$ and HFBBA; and mixtures thereof.

$[Co_3(INA)_4(O)-(C_2H_5OH)_3][NO_3] \cdot C_2H_5OH \cdot 3H_2O$, which may be produced from $Co(NO_3)_2 \cdot 6H_2O$, isonicotinic acid (INA), and ethanol. $[Co_3 (FINA)_4(O)-(C_2H_5OH)_2] \cdot H2O$, which may be produced from $Co(NO_3)_2 \cdot 6H_2O$, 3-fluoro-isonicotinic acid (FINA), and ethanol. $[Co(INA)_2]$ DMF, which may be produced from $Co(NO_3)_2 \cdot 6H2O$, isonicotinic acid (INA), and DMF. $[Co(FINA)_2]H2O$, which may be produced from $Co(NO_3)_2 \cdot 6H2O$, 3-fluoro-isonicotinic acid (FINA), and DMF.

Additional MOFs of the present invention include, but are not limited to: $[Ni_3(\mu_3\text{-btc})_2(\mu_4\text{-btre})_2(\mu\text{-H}_2O)_2]n \cdot H_2O$, where n is ~22, which may be produced from benzene-1,3, 5-tricarboxylate (btc) and 1,2-bis(1,2,4-triazol-4-yl)ethane (btre). $\{[Cu_2(BPnDc)2(bpy)] \cdot 8DmF \cdot 6H_2O\}n$. [DHTP-Ni]

Additional MOFs of the present invention include, but are not limited to (Fe3O(BDC)3X, X=Cl, OH, BDC=1,4-benzenedicarboxylate); Fe-BTC (iron 1,3,5-benzenetricarboxylate); iron azobenzenetetracarboxylate; Fe6O2(Tazb) 3X2, X=Cl, OH, Tazb=3,3',5,5'-azobenzenetetracarboxylate.

Additional MOFs of the present invention include, but are not limited to variants of M-MOF-74 (MOF-74(M)), where the M=Zn, Fe, Ni, Co, Mg, Mn, and mixtures thereof, and where the linker is 2,5 dihydroxyterephthalic acid (DHTA).

Additional MOFs of the present invention include, but are not limited to MOFs prepared using one or more of the following linkers: 1,2,4,5-Tetrakis(4-carboxyphenyl)benzene; 1,2,4,5-Tetrakis(4-carboxyphenyl)benzene; 1,3,5-Tris (4-carboxyphenyl)benzene; 2,5-Dihydroxyterephthalic acid; 2,6-Naphthalenedicarboxylic acid; 2-Hydroxyterephthalic acid; 2-Methylimidazole; 3,3',5,5'-Tetracarboxydiphenylmethane; 4,4',4"-s-Triazine-2,4,6-triyl-tribenzoic acid; 9,10-Anthracenedicarboxylic acid; Biphenyl-3,3',5,5'-tetracarboxylic acid; Biphenyl-3,4',5-tricarboxylic acid; Imidazole; Terephthalic acid; Trimesic acid; [1,1':4',1"]Terphenyl-3,3', 5,5'-tetracarboxylic acid.

Additional MOFs of the present invention include, but are not limited to: $[Cu(Hoxonio)(4,4'-bipy)_{0.5}]$; [Cu(bdc-OH)]; $[Zn_2(tcom)]$; $[Zn_2(tcom)]$; $[Zn_4O(bdc)(btb)_{4/3}]$; $[Zn_8(bhfp)_{33}]$; $[Zn_2(BPnDC)_2(4,4'-bipy)]$; $[Zn(mIm)_2]$; $[Cu(1,4-ndc)]$; $[Cu_2(ebtc)_3]$; $[Cu_2(Hbtb)_2]$; $[Ni_2(dhtp)]$; [Cu-BTC]; $[Zn(bIm)(nIm)]$; $[Zn(cbIm)(nIm)]$; $[Zn(Im)_{1.13}(nIm)_{0.87}]$; $[Zn(nbIm)(nIm)]$; $[Zn(mbIm)(nIm)]$; $[Zn(bbIm)(nIm)]$; $[Zn(cnIm)(nIm)]$; $[Zn(pydc)(dma)]$; $[Cu_3(btc)_2(H_2O)_x]$; $[Zn_2(bttb)(dma)_2]$; $[Zn_2(bttb)]$; $[Zn_2(bttb)(py-CF_3)_2]$; $[Ni^{III}_2Ni^{III}(3-OH)(pba)_3(2,6-ndc)_{1.5}]$; $[Al(OH)(2,6-ndc)]$; $[Zn_4O(fma)_3]$; $[[H_3O][Zn_7(\mu_3-OH)_3(bbs)_6]]$; $[Al_4(OH)_8[btec]]$; $[Mg(tcpbda)]$; $[Sc_2(bdc)_3]$; $[Zn(bdc)(4,4'-bipy)_{0.5}]$; $[Zn_3(OH)(p\text{-cdc})_{2.5}]$; $[Zn_3(OH)(p\text{-cdc})_{2.5}(DMF)_4]$; $[Cr_3F(H_2O)_3O(btc)_2]$; $[Cr_3F(H_2O)_2O(bdc)_3]$; [Cu-BTC]; [β-Zn (F-pymo)_2]; [β-Co(F-pymo)_2]; [Cu(H-pymo)_2]; $[Zn_2(cnc)_2(dpt)]$; $[Zn(dtp)]$; $[Zn_2(2,6-ndc)_2(dpni)]$; $[Zn_2(2,6-ndc)_2(dpni)]$; $[Ni_2(pbmp)]$; $[Zn(abdc)(bpee)_{0.5}]$; [Cu(fma) $(bpee)_{0.5}]$; $[Co_3(2,4-pdc)_2(\mu_3-OH)_2]$; $[H_2[Ni_3O(H_2O)_3(tatb)_2]$; $[Zn_3(ntb)_2]$; $[Zn(Pur)_2]$; [Cr(OH)(bdc)]; [Cr(OH) $(bdc)(H_2O)]$; $[Mn(2,6-ndc)]$; $[Cr_3O(H_2O)_2F(ntc)_{1.5}]$; [Mn $(HCOO)_2]$; $[Cu(dhbc)_2(4,4'-bipy)]$; [Cu(tip)]; $[Zn_5(bta)_6(tda)_2]$; $[Zn_4(OH)_2(1,2,4-btc)_2]$; $[Cu(pmc)_2]$; [Zn(1,4-ndc) (bpe)]; $[Cu_2(pzdc)_2(4,4'-bipy)]$; [Zn(dabco)(3,3'tpdc)]; $[Zn_2(tcom)]$; $[Zn_2(tcom)]$; $[Zn_8(bhfp)_{33}]$; $[CO_2(ad)_2(OAc)_2]$; $[Co[Fe(Tp)(CN)_3]_2]$; $[[Cu_5(Tz)_9](NO_3)]$; [Zn(H_2O)(BenzTB)]; $[Ni_2(dhtp)]$; [Zn(bIm)(nIm)]; [Zn(cbIm)(nIm)]; $[Zn(Im)_{1.13}(nIm)_{0.87}]$; [Zn(nbIm)(nIm)]; [Zn(mbIm)(nIm)]; [Zn (bbIm)(nIm)]; [Zn(cnIm)(nIm)]; [Zn(pydc)(dma)]; [Fe(pz) Ni(CN)_4]; $[Cu(btc)H_2O_{(0.5/Cu)}]$; $[Zn_2(bttb)(dmf)_2]$; $[Zn_2(bttb)]$; $[Zn_2(bttb)(py-CF_3)_2]$; $[Sc_2(bdc)_3]$; $[H_3[(Cu_4Cl)_3(BTTri)_8]]$; $[H_3[(Cu_4Cl)_3(BTTri)_8](en)_{1.25}]$; [Zn(bdc)(4,4'-bipy)_{0.5}]; [Zn_2(tcom)(4,4'-bipy)]; $[Cu(fma)(bpee)_{0.5}]$; $[Cd_3(OH)_2(apta)_4]$; $[Cr_3O(H_2O)_2F(ntc)_{1.5}]$; $[Mn(HCOO)_2]$; $[Zn_2(Atz)(ox)]$; $[[Ni(bpe)_2(N(CN)_2)](N(NC)_2)]$; [Al(OH) (bpydc)]; $[Al(OH)(bpydc) \cdot 0.97Cu(BF_4)_2]$; $[Cu_3(btei)]$; $[Cu_3(tpbtm)]$; where the ligands of these MOFs are defined as: H2bhfp=2,2'-bis(4-carboxyphenyl)hexafluoropropane; F-pymo=5-fluoropyrimidin-2-olate; H-pymo=pyrimidin-2-olate; pbmp=N,N'-piperazinebismethylenephosphonate; Pur=Purinate; H3oxonic=4,6-dihydroxy-1,3,5-triazine-2-carboxylic acid; H2bdc-OH=2-hydroxybenzene-1,4-dicarboxylic acid; H4tcom=tetrakis[4-carboxyphenyl)oxamethyl]methane; BPnDC=benzophenone 4,4'-dicarboxylicacid; 1,4-ndc=1,4-naphthalenedicarboxylate; ebtc=1,10-ethynebenzene-3,3',5,5'-tetracarboxylate; Im=imidazolate; mIm=2-methylimidazolate; nIm=2-nitroimidazolate; bIm=benzimidazolate; cbIm=5-chlorobenzimidazolate; nbIm=5-nitrobenzimidazolate; mbIm=5-methylbenzimidazolate; bbIm=5-bromobenzimidazolate; cnIm=4-cyanoimidazolate; pydc=3,5-pyridinedicarboxylate; dma=N,N"-dimethylacetamide; fma=fumarate; H2bbs=4,4'-bibenzoic acid-2,2'-sulfone; btec=1,2,4,5-benzenetetracarboxylate; H2tcpbda=N,N,N',N'-tetrakis(4-carboxyphenyl)-biphenyl-4,4'-diamine; p-cdc=deprotonated form of 1,12-dihydroxydicarbonyl-1,12-dicarba-closo-dode-caborane; cnc=4-carboxycinnamic; dpt=3,6-di-4-pyridyl-1,2,4,5-tetrazine; dtp=2,3-di(tetrazolate-5-yl)pyrazine; abdc=4,4'-azobenzenedicarboxylate; 2,4-pdc=pyridine-2,4-dicarboxylate; tatb=represents-4,4',4"-s-triazine-2,4,6-triyl-tribenzoate; ntb=4,4',4"-nitrilotrisbenzoate; ntc=naphthalene-1,4,5,8-tetracarboxylate; dhbc=2,5-dihydroxybenzolate; 3,3'-tpdc=terphenyl-3,3'-dicarboxylate; Tp=hydrotris(pyrazolyl) borate; Tz=tetrazolate; BenzTB=N,N,N',N'-benzidinetetrabenzoate; pz=pyrazine; apta=4-aminophenyltetrazolate; bpydc=2,2'-bipyridine-5,5'-dicarboxylate; btei=5,5',5''-benzene-1,3,5-triyltris(1-ethynyl-2-isophthalate); tpbtm=N,N',N"-tris(isophthalate)-1,3,5-benzenetricarboxamide; tip=5-(1H-tetrazol-1-yl)isophthalate; Hbta=1,2,3-benzenetriazole; tda=thiophene-2,5-dicarboxylate; 1,2,4-btc=benzene-1,2,4-tricarboxylate; pmc=pyrimidine-5-carboxylate; 3,5-pdc=pyridine-3,5-dicarboxylate. Other MOFs produced using these ligands are also envisioned.

In a preferred embodiment of the present invention, the MOF has a secondary linkage. The MOF of the present invention may be produced from a partially fluorinated linker, particularly one or more of those shown in formulas 1 and 2.

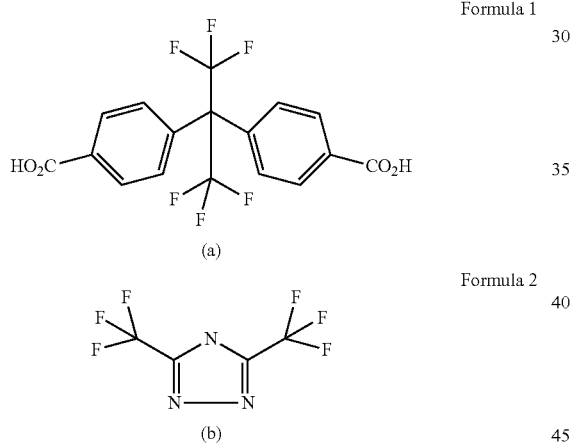

The MOFs of the present invention may be produced from a non-fluorinated linker, particularly one or more of those shown in Formula 3 and 4.

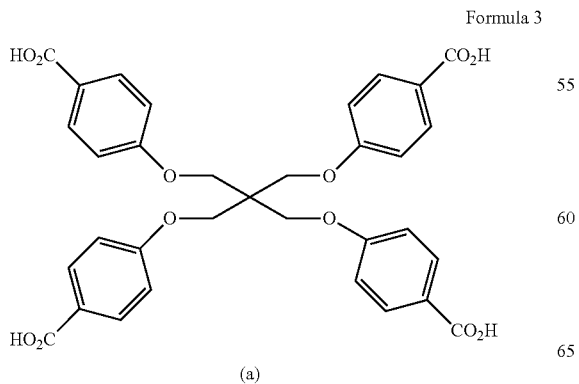

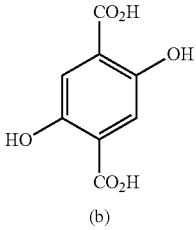

The MOFs of the present invention may be produced from a non-fluorinated linker, particularly one or more of those shown in Formula 5, 6, and 7.

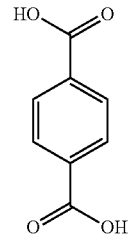

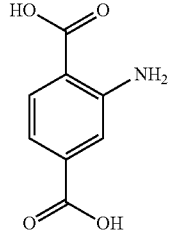

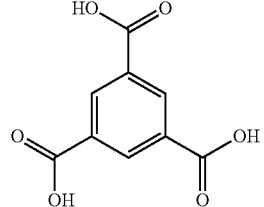

The MOFs of the present invention may be produced with zinc nitrate or DMF (dimethylformamide).

In a preferred embodiment of the present invention, the MOF is produced with zinc nitrate, DMF, and at least one fluorinated or non-fluorinated linker, particularly at least one of those shown in Formulas 1, 2, 3, 4, 5, 6, and 7.

In an embodiment of the present invention, the COFs may be produced from one or more compounds of Formula 8, 9, 10, 11, 12, 13 and 14.

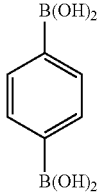

Formula 9
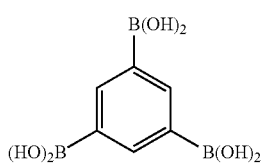
Formula 10
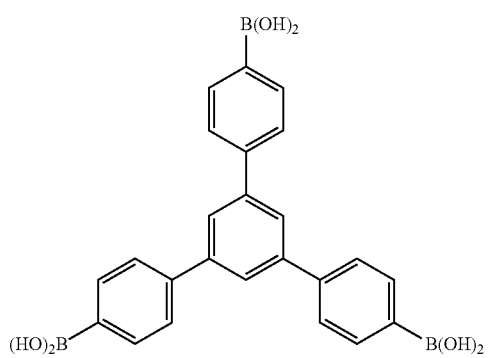
Formula 11
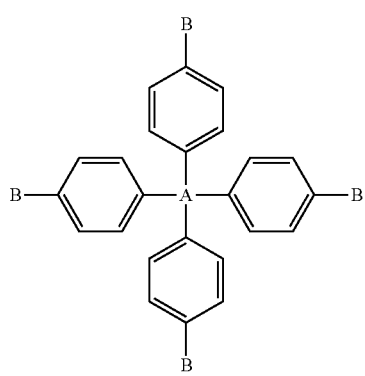
where A = carbon, adamantine,
B = Br, acetylene
Formula 12
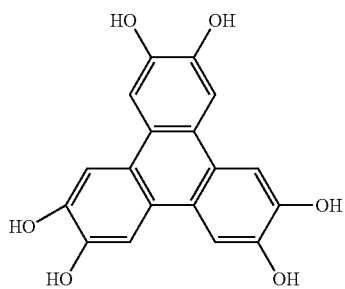
Formula 13
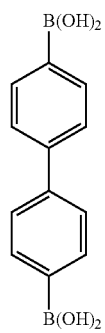
Formula 14
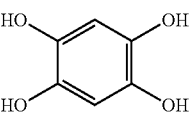
In another embodiment of the present invention, the COFs are selected from the group consisting of COF-8, COF-10, COF-12, COF-16, and mixtures thereof. COF-8, COF-10, COF-12, and COF-16 may be produced according to Formula 15 a), b), c), and d) respectively.
Formula 15
a)
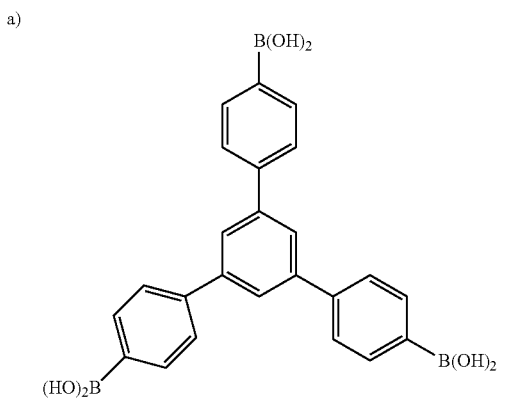
b)

-continued (c) 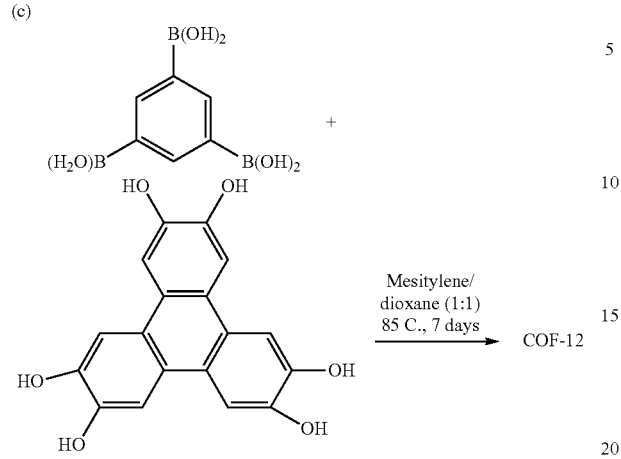

d) 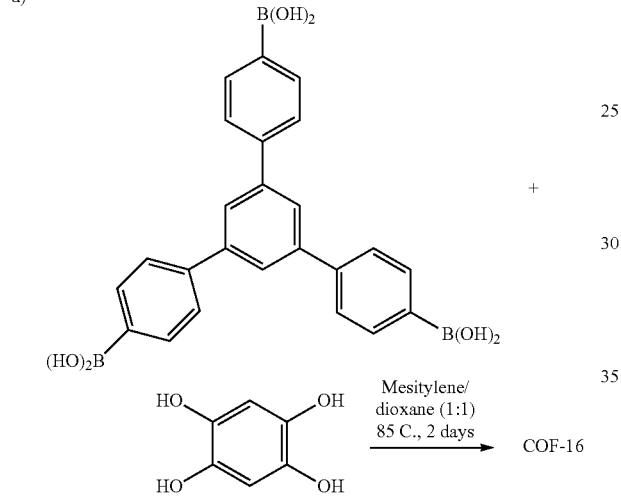

Exemplary COFs are set forth in Table A. The building units for the exemplary COFs set forth in Table A are set out in formulas 16-46. For example, dehydration of 1,4-benzenediboronic acid (COF-1), dehydration of 1,4-benzenediboronic acid (COF-1) with hexahydroxytriphenylene (COF-5)

TABLE A

| Material | Building Units |
|---|---|
| COF-1 | 16 |
| COF-5 | 16 + 36/37 |
| COF-6 | 32 + 36 |
| COF-8 | 34 + 36 |
| COF-10 | 19 + 36/37 |
| COF-11 | 32 + 29d |
| COF-14 | 32 + 29c |
| COF-16 | 32 + 29b |
| COF-18 | 32 + 29a |
| COF-42 | 25 + 33 |
| COF-43 | 25 + 35 |
| COF-66 | 45a + 30a |
| COF-105 | 41 + 36 |
| COF-108 | 42 + 36 |
| COF-202 | 31 + 41 |
| COF-300 | 38 + 21 |
| COF-366 | 46 + 21 |
| COF-A (CTF-1) | 22 |
| COF-B (CTF-2) | 23 |

Formulas 16-46

22
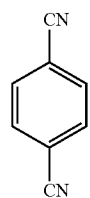
23
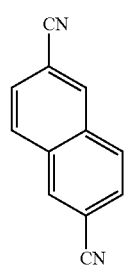
24
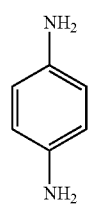
25
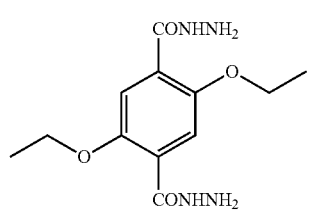
26
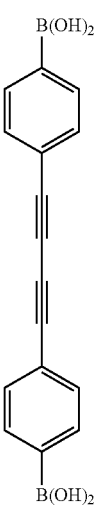
27
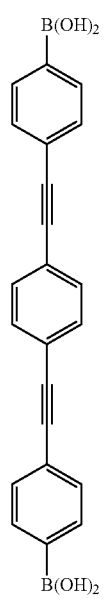
28
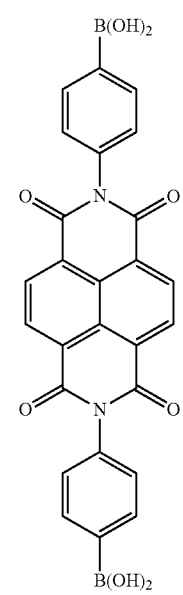
29
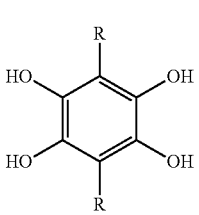
a) R = H
b) R = CH₃
c) CH2CH3
d) R = CH₂CH₂CH₃

30
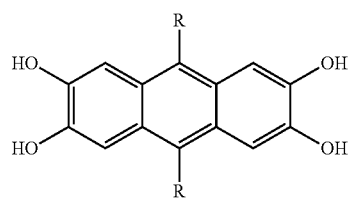
a) R = H
b) R = CH$_3$
31
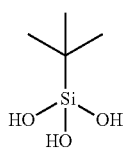
32
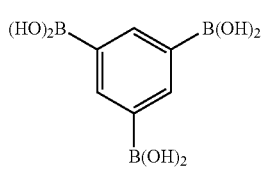
33
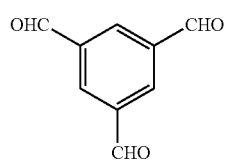
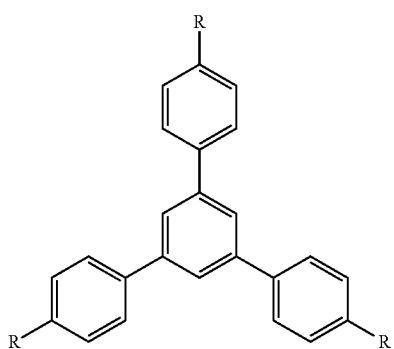
R = B(OH)$_2$   34
R = CHO         35
36
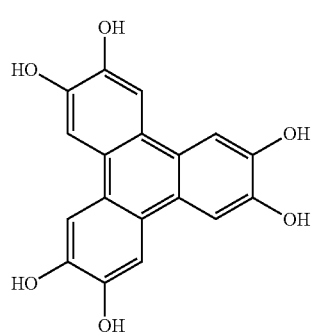
37
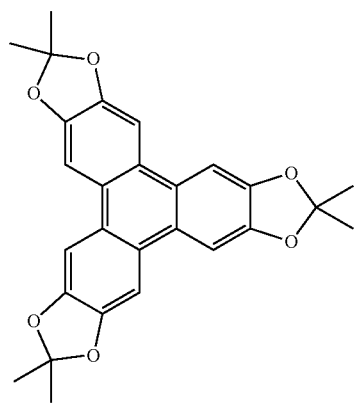
38
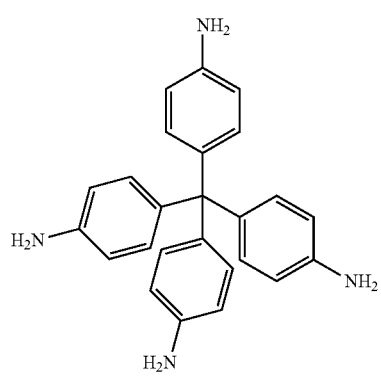
39
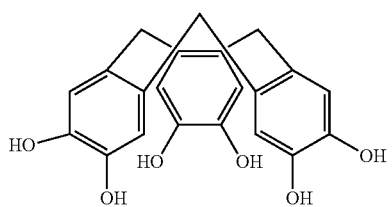
40
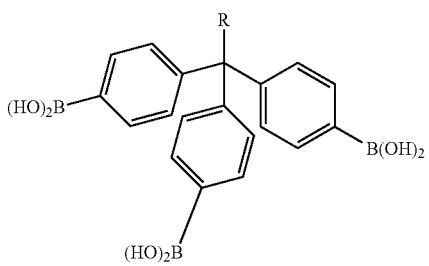
R = (CH$_2$)$_{11}$CH$_3$   40a
R = alyl                     40b -continued

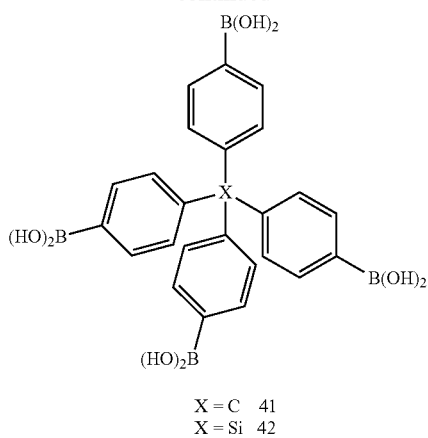

X = C  41
X = Si  42

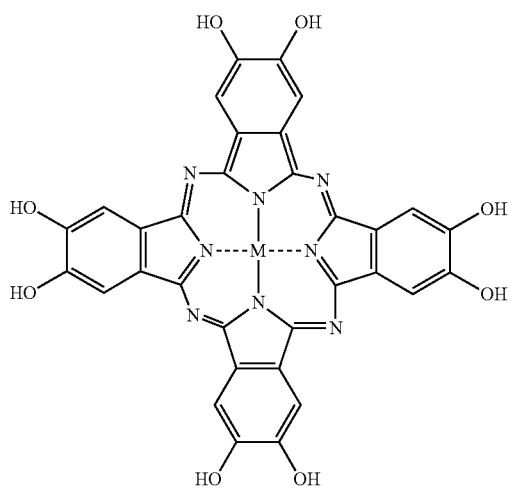

a) M = Ni
b) M = Zn

43

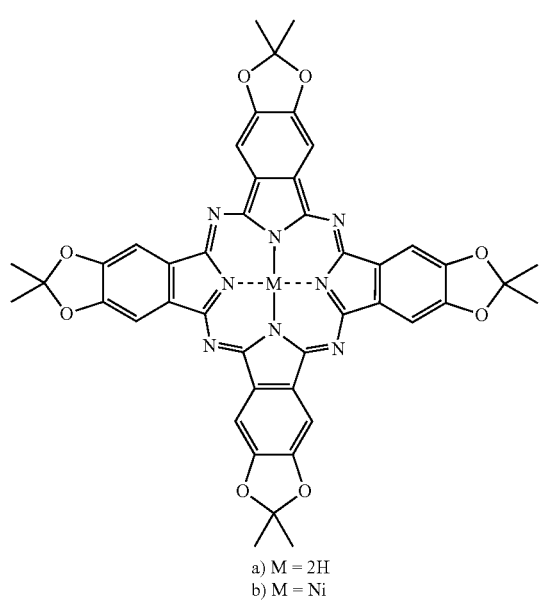

a) M = 2H
b) M = Ni

44

-continued

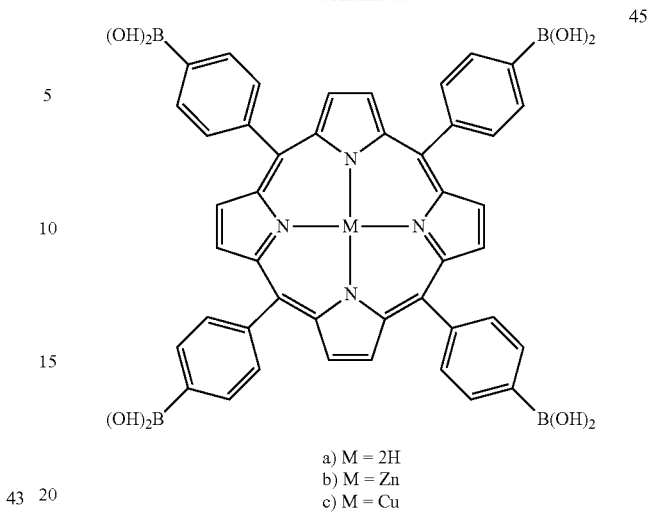

a) M = 2H
b) M = Zn
c) M = Cu

45

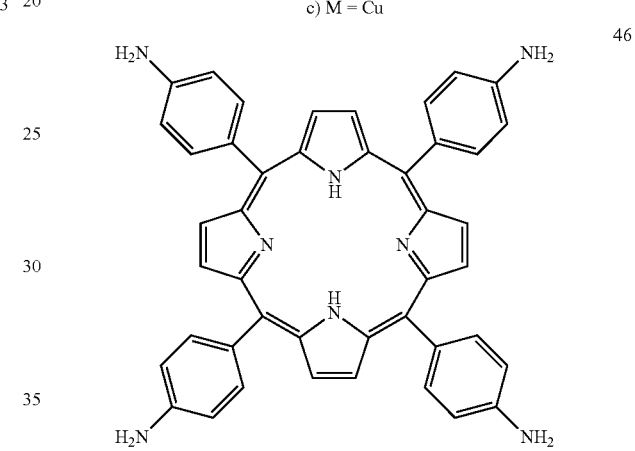

46 approximately or greater than 11 Å. In another embodiment of the present invention, the MOF has cavities approximately or greater than 24 Å. In another embodiment of the present invention, the MOF has cavities approximately or greater than 29 Å.

In a highly preferred embodiment of the present invention, the MOF is selected from MIL-101, derivatives of MIL-101, MIL-100, derivatives of MIL-100, and mixtures thereof, In an embodiment of the present invention, the fluid or air temperature produced by the chiller is in the range of 30° F. to 60° F. In another embodiment of the present invention, the fluid or air temperature produced by the chiller is in the range of 33° F. to 55° F. In another embodiment of the present invention, the fluid or air temperature produced by the chiller is in the range of 44° F. to 54° F. In an embodiment of the present invention, the fluid or air temperature produced by the chiller is greater than 30° F. In an embodiment of the present invention, the fluid or air temperature produced by the chiller is less than 80° F.

In an embodiment of the present invention, the cool fluid temperature is in the range of 55° F. to 180° F. In another embodiment of the present invention, the cool fluid temperature is in the range of 65° F. to 130° F. In another embodiment of the present invention, the cool fluid temperature is in the range of 75° F. to 120° F. In another embodiment of the present invention, the cool fluid temperature is in the range of 80° F. to 110° F. In another embodiment of the present invention, the cool fluid temperature is in the range of 85° F. to 100° F. In an embodiment of the present invention, the cool fluid temperature is in greater than 50° F. In an embodiment of the present invention, the cool fluid temperature is less than 200° F.

In an embodiment of the present invention, the hot fluid temperature is in the range of 100° F. to 600° F. In another embodiment of the present invention, the hot fluid temperature is in the range of 120° F. to 500° F. In another embodiment of the present invention, the hot fluid temperature is in the range of 130° F. to 400° F. In another embodiment of the present invention, the hot fluid temperature is in the range of 140° F. to 300° F. In another embodiment of the present invention, the hot fluid temperature is in the range of 150° F. to 250° F. In another embodiment of the present invention, the hot fluid temperature is in the range of 160° F. to 220° F. In another embodiment of the present invention, the hot fluid temperature is in the range of 170° F. to 210° F. In another embodiment of the present invention, the hot fluid temperature is in the range of 175° F. to 200° F. In another embodiment of the present invention, the hot fluid temperature is in the range of 180° F. to 195° F. In an embodiment of the present invention, the hot fluid temperature is greater than 90° F. In an embodiment of the present invention, the hot fluid temperature is less than 600° F.

The heat transfer systems of the present invention may comprise one, two, or more individual heat transfer systems for heating or cooling. For example, multiple adsorption chiller units may be combined in a parallel; one motivation for such a configuration is to increase the overall cooling capacity. In another embodiment of the present, two or more adsorption chiller units may be connected in series. In another embodiment of the present invention chiller systems employing two or more stages are utilized where one of the stages utilizes an adsorption chiller where the sorbent is an MOF of the present invention and the working fluid is a working fluid of the present invention. One motivation for a staged chiller design is to drive the output temperature at each subsequent stage to lower temperatures for uses including but not limited to applications such a refrigeration, freezing, gas separations, and cryogenic cooling. In another embodiment of the present invention, the chilled fluid output from one chiller stage is used to cool the adsorber of a second chillier stage. In another embodiment of the present invention, the first stage is an adsorption chiller unit where the sorbent is selected from silica gel, carbon black, zeolites, or mixtures thereof, and the working fluid is selected from carbon dioxide or water. In another embodiment of the present invention, stage 2 is an adsorption chiller unit where the sorbent is a MOF of the present invention and the working fluid is a working fluid of the present invention, preferrably a fluorinated working fluid. In another embodiment of the present invention, stages 1 and 2 are adsorption chiller units where the sorbents in each unit are MOFs of the present invention and the working fluids are a working fluids of the present invention, preferrably a fluorinated working fluids. In another embodiment of the present invention, one or more of the stages is an absorption chiller system, such as a water-Lithium bromide system or a water-ammonia system. In another embodiment of the present invention, one or more of the stages is a vapor compression chiller system. In a vapor compression system, different types of compressors can be used including, but not limited to, rotary compressors, reciprocating compressors, screw compressors, or, particularly, centrifugal compressors. Centrifugal compressor can be used in one or more stages or a mini-centrifugal compressor can be used. The compressor can be driven by an electric motor or a gas turbine (for example fed by the exhaust gases of a vehicle, for mobile applications) or gear driven. The installation may include a coupling of the regulator with a turbine to generate electricity (Rankine cycle). In an embodiment of the present invention, refrigerant desorbed from a bed undergoing thermal regeneration may be passed through a compression device for the purpose of superheating the refigerant prior to passing through another bed undergoing thermal regeneration thus using the heat of compression to enhance desorption. In an embodiment of the present invention, refrigerant desorbed from a bed undergoing thermal regeneration may be passed through an expansion device, such as but not limited to a throttling valve or turboexpander for the purpose of pre-chilling the refrigerant before passing through an evaporator or another sorption bed in the adsorption portion of its cycle. The expansion device may also produce auxiliary electrical power in the cycle.

Certain metal organic framework (MOF) compounds exhibit super-hydrophilic properties. Super hydrophilic materials are able to absorb water to densities that approach the liquid state but at conditions well under the saturated vapor pressure and temperature where liquid water condenses. The mass loadings for these (or similar) MOFs represent an extraordinary improvement relative to silica gel that is used in commercial adsorption chillers and can be used to improve the efficiency and reduce the size and cost of current chillers. The very high mass loading may be at relative saturation vapor pressures that are too high to be useful in the adsorption cycle of standard HVAC systems where the adsorption bed can only be cooled to 30° C. A double effect adsorption chiller design has been conceived that separates the chiller into 4 chambers instead of two and divides the cooling load between the two chambers. A preferred embodiment would use a fluorophilic MOF and any suitable fluorochemical working fluid, including but not limited to CFCs, HFCs, or HFOs, HCFOs, HFEs, in stage 1. Stage 1 would reduce the adsorption bed temperature in stage 2 below the standard temperature of 30° C. By lowering or pre-cooling the adsorption bed in stage 2, the P/Po in adsorption mode can be increased sufficiently to achieve optimal mass loading of water in a super-hydrophilic sorbent or other sorbent-refrigerant pair chosen for the stage 2 chiller. The double effect adsorption chiller can take advantage of extremely high mass loadings of water in super-hydrophilic MOFs and fluorochemical refrigerants with fluorophilic MOF sorbents that are not possible with current single effect adsorption chiller designs.

Figure 3:
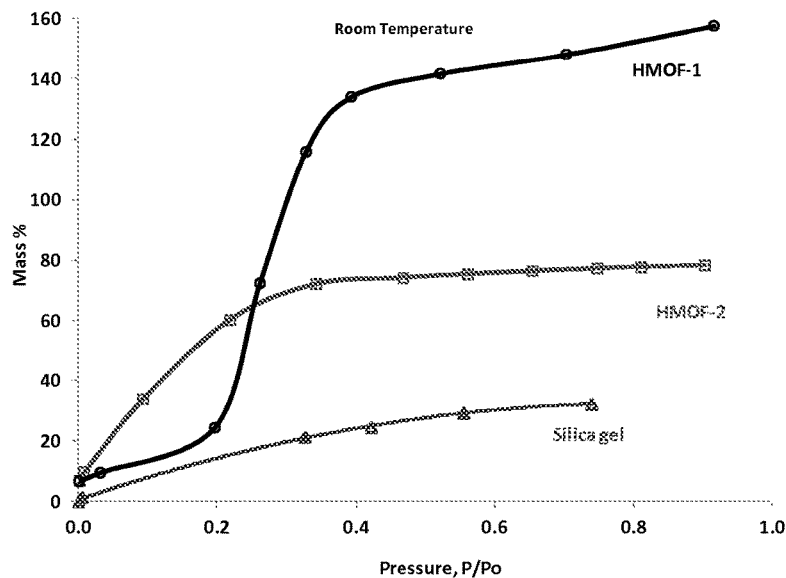
FIG. 3 is a graph of the room temperature isotherms for two super hydrophilic MOFs and silica gel.
Figure 4:
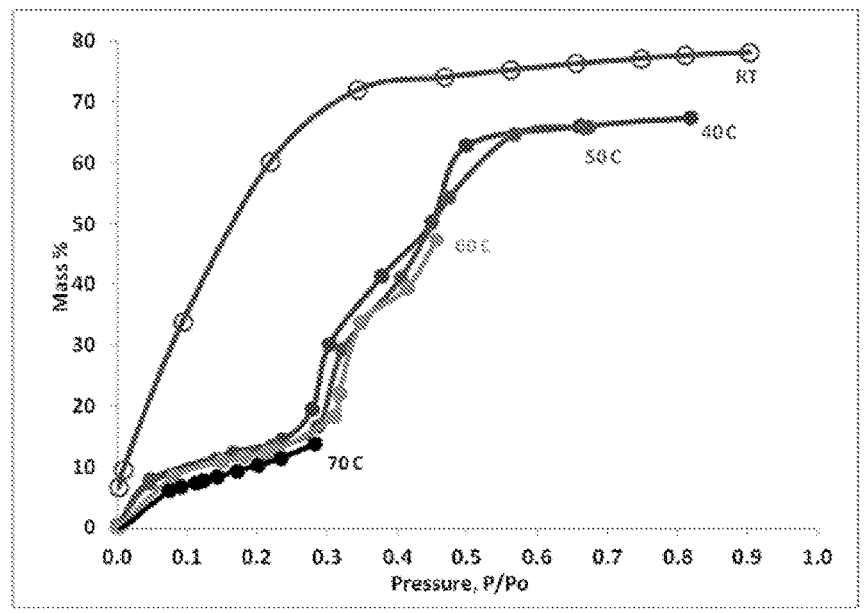
FIG. 4 is a graph of temperature dependent adsorption isotherms for water in MIL-100.

Metal organic framework (MOF) compounds that exhibit super-hydrophilic properties are able to absorb water to densities that approach the liquid state but at conditions well under the saturated vapor pressure and temperature where liquid water condenses. FIG. 3 shows an example of two super hydrophilic MOFs and their adsorption isotherms at room temperature. An adsorption isotherm for silica gel is provided for comparison. The mass loadings for these (or similar) MOFs represent an extraordinary improvement relative to silica gel that is used in commercial adsorption chillers. FIG. 4 shows the temperature-dependent set of isotherms measured for MIL-100. The adsorption beds in the chillers reach a minimum temperature of about 30° C. near the end of an adsorption cycle. The adsorption bed must pull water off the evaporator at a temperature of 7° C. and pressure of 9 mbar, just under the saturation vapor pressure of 10 mbar. At 30° C., the saturation vapor pressure is 42.5 mbar. Hence, the sorbent must reach a high mass loading of water at a P/Po=9/42.5=0.21. As illustrated in FIGS. 3 and 4, the shoulder of the isotherms are at higher P/Po than 0.21, making the materials only marginally better than silica gel under these conditions.

Figure 5A:
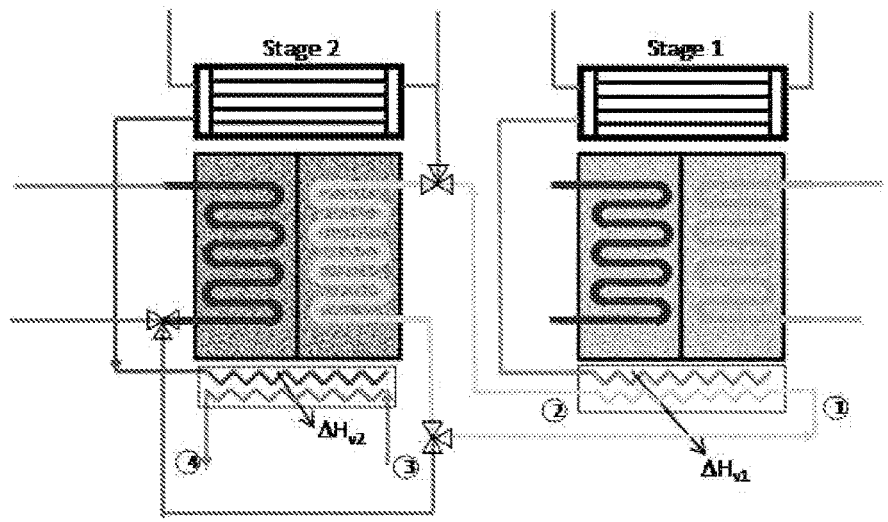
FIG. 5a is a double effect hybrid adsorption chiller.

A double effect adsorption chiller design has been conceived which separates the chiller into 4 chambers instead of two and divides the cooling load between the two chambers. A design for the chiller is provided in FIG. 5a. In one embodiment, the stage 1 chiller operates with a fluorophilic MOF sorbent and a fluorinated working fluid, including but not limited to an CFC, HFC, or HFO, HCFO (such as HFO-1234yf, HFO-1234ze, HFO-1336mzz, HCFO-1233zd), or HFE. For example, refrigerant R-123 could be chosen for stage 1. The evaporator would operate at a pressure of approximately 0.75 bar, sufficient to deliver refrigerant at state point 2 at 20° C. to provide initial cooling for stage 2. The condenser would operate at standard conditions of 30° C. and Po=1.1 bar. Hence, the P/Po during adsorption mode would be P/Po=0.75/1.1=0.68. Desorption could occur at virtually any temperature sufficient to unload the refrigerant from the sorbent. At the standard operating condition of 90° C., Po=6.24 bar. Hence, desorption bed P/Po=1.1/6.24=0.18. Any suitable sorbent refrigerant pair could be chosen for stage 1 to lower the adsorption bed temperature in stage 2 below the standard temperature of 30° C. By lowering or pre-cooling the adsorption bed in stage 2, the P/Po in adsorption mode can be increased sufficiently to achieve optimal mass loading of water in a super-hydrophilic sorbent or other sorbent-refrigerant pair chosen for the Stage 2 chiller.

Figure 5B:
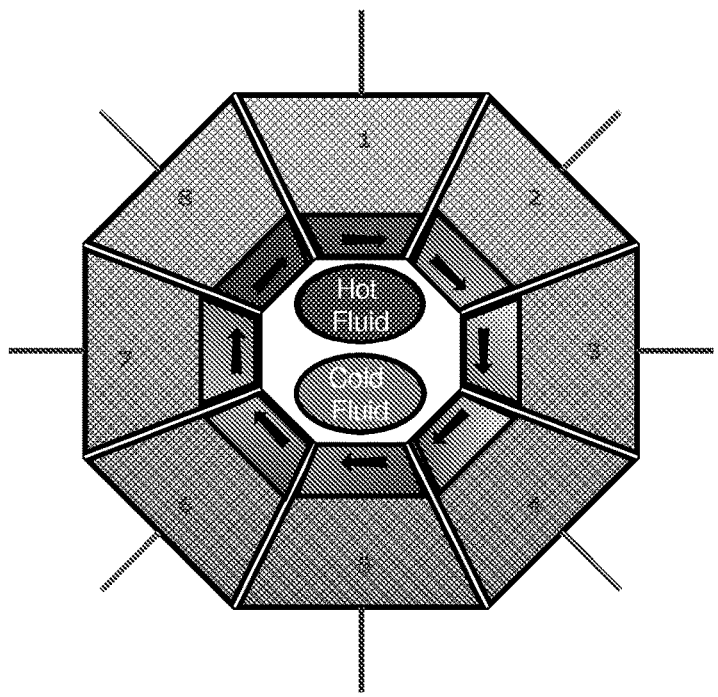
FIG. 5b is a chain configuration staged adsorption chiller.
Figure 6:
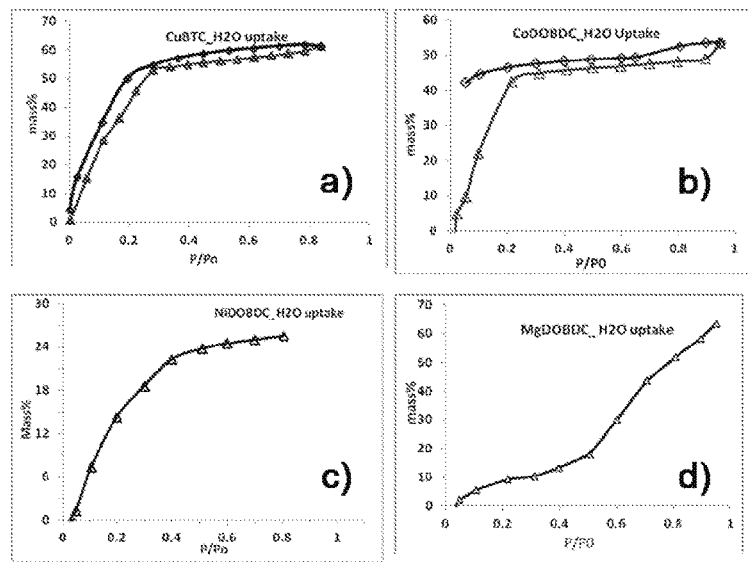
FIGS. 6a, 6b, 6c and 6d are graphs of water adsorption in mass % versus P/Po.
Figure 7:
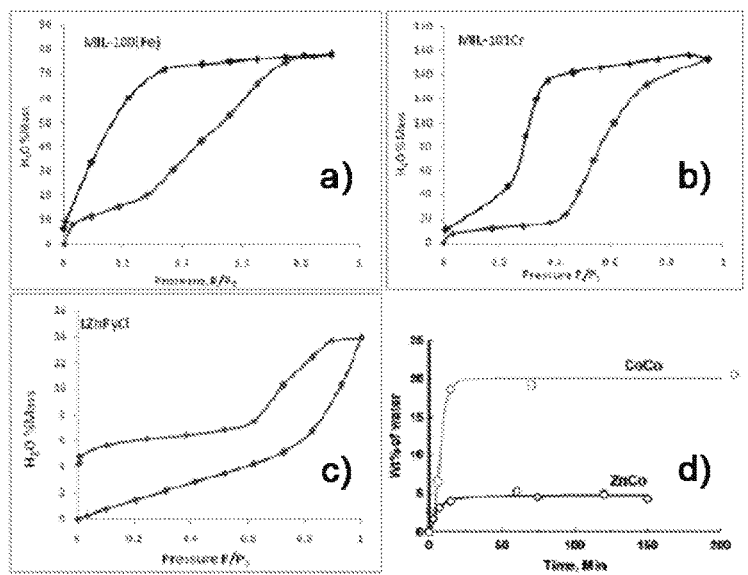
FIGS. 7a, 7b, 7c and 7d are graphs of water adsorption in mass % versus P/Po.

In another embodiment of the staged chiller invention, adsorption modules may be integrated in a chain configuration as illustrated in FIG. 5b. The design is a heat engine where each wedge in the octagon represents an adsorption bed. Heat flows, such as in a clockwise direction by using valves to switch the inlets and outlets between evaporator/condenser and heat/cooling sources. This embodiment produces a virtual rotation of the beds with temperature increasing as a bed "moves" from position 5 to position 1 and decreases as it continues from position 1 back to position 5. Heat is effectively recuperated from the beds being heated to beds being cooled through a heat transfer fluid flowing sequentially through the beds. Heat is added to the fluid prior to position 1 and removed prior to position 5. FIG. 5b shows a configuration with 8 beds, but any even number of beds will work with 6 beds being the minimum needed for continuous refrigerant flow. Adsorption beds may utilize microchannel heat exchanger designs to improve heat transfer properties. In addition, the device may contain beds with the same sorbent-refrigerant combination or different combinations of sorbent-refrigerant pairs to obtain different output temperatures from the device.

The present inventors discovered that certain combinations of specific MOFs with specific working fluids are particularly useful for heat transfer operations such as adsorption chilling or heating. Without wishing to be bound by any particular scientific theory, it is believed the very high mass loadings and relatively low heats of adsorption that are possible with certain combinations of working fluids and MOFs permit highly efficient adsorption heat transfer systems for heating or cooling, with relatively high coefficient of performance (COP). In certain systems, a high achievable mass loading per volume of sorbent permits reduction in the size of the system.

In some embodiments of the present invention, the adsorption heat transfer system is coupled to an external heat source using a circulated heat transfer fluid. Exemplary external heat sources include, but are not limited to, solar collectors, boilers, furnaces, water heaters, internal combustion engines, electric motors, compressors, geo-thermal heat sources, reactors, distillation columns, refineries, solar ponds, steam engines, power plants, data centers, bio-mass furnace, cement plant, pre-heaters, rotary kilns, food dryers, incinerators, paper mills, steam, thermal oil, and the like.

The working fluids of the present invention may comprise one or more of hydrofluorocarbons (HFCs), hydrofluoroolefins (HFOs), hydrocarbons, hydrochlorofluoroolefins (HFCOs), chlorofluorocarbons (CFCs), hydrochlorofluorocarbons (HCFCs), hydrofluoroethers (HFEs), C1 to C5 alcohols, C1 to C4 aldehydes, C1 to C4 ketones, C1 to C4 ethers and diethers, dimethyl ether, methyl formate, methylal, carbon dioxide, trans-1,2-dichloroethylene, R-14, water, atmospheric gases, including nitrogen and oxygen, and mixtures thereof More specific examples of the workings fluids include:

(a) hydrofluorocarbons (HFCs) can include, but are not limited to C1 to C5 alkanes possessing at least one fluorine and at least one hydrogen; preferably trifluoromethane (HFC-23); difluoromethane (HFC-32); 1,1,1,2,2-pentafluoroethane (HFC-125); 1,1,2,2-tetrafluorothane (HFC-134); 1,1,1,2-tetrafluoroethane (HFC-134a); 1,1,1-trifluoroethane (HFC-143a); 1,1,2-trifluoroethane (HFC-143); 1,1-difluoroethane (HFC-152a); 1,2-difluoroethane (HFC-152); fluoroethane (HFC-161); 1,1,1,2,3,3,3-heptafluoropropane (HFC-227ea); 1,1,1,3,3-pentafluoropropane (HFC-245fa); 1,1,1,2,3-pentafluoropropane (HFC-245eb); 1,1,2,2,3-pentafluoropropane (HFC-245ca); 1,1,1,3,3,3-hexafluoropropane (HFC-236fa); 1,1,1,3,3-pentafluorobutane (HFC-365mfc) and 1,1,1,2,2,3,4,5,5,5-decafluoropentane (HFC-4310mee), and mixtures thereof. Preferably the HFC is non-flammable, including, but not limited to, HFC-134a, HFC-245fa, HFC-227ea, HFC-125, HFC-4310mee, HFC-236fa, and mixtures thereof. Even more preferably the HFC is HFC-134a, HFC-245fa, and mixtures thereof.

(b) hydrofluoroolefins can include, but are not limited to pentafluoropropenes (HFO1225), tetrafluoropropenes (HFO1234), trifluoropropenes (HFO1243), all tetrafluorobutene isomers (HFO1354), all pentafluorobutene isomers (HFO1345), all hexafluorobutene isomers (HFO1336), all heptafluorobutene isomers (HFO1327), all heptafluoropentene isomers (HFO1447), all octafluoropentene isomers (HFO1438), all nonafluoropentene isomers (HFO1429), and mixtures thereof; preferably (cis and/or trans)-1,2,3,3,3-pentafluoropropene (HFO-1225ye), 3,3,3-trifluoropropene (HFO-1243zf), (cis and/or trans)-1,3,3,3-tetrafluoropropene (HFO-1234ze), 2,3,3,3-tetrafluoropropene (HFO-1234yf), (cis and/or trans)-1,1,1,3,3,3-hexafluorobutene (HFO-1336mzz) In a preferred embodiment of the present invention the working fluid is preferably HFO-1234yf, HFO-1234ze (particularly the trans-isomer) or HFO-1336mzz.

(c) hydrocarbons can include, but are not limited to hexane, pentane isomers, butane isomers, propane; preferably n-pentane, cyclopentane, iso-pentane. Butane is preferably isobutane or n-butane. Though not preferred in this application due to their high flammability, it is understood that hydrocarbons may be present.

(d) C1 to C5 alcohols, C1 to C4 aldehydes, C1 to C10 ketones and fluoroketones, C1 to C4 ethers and diethers. An exemplary fluoroketone is 1,1,1,2,2,4,5,5,5-nonafluoro-4 (trifluoromethyl)-3-pentanone (e) HCFOs can include, but are not limited to, (cis and/or trans) 1-chloro-3,3,3-trifluoropropene, particularly the trans-isomer, 2-chloro-3,3,3-trifluoropropene (HCFO-1233xf) and dichlorotrifluoropropene (HCFO1223); and mixtures thereof. In a preferred embodiment of the present invention the working fluid is preferably HCFO-1233zd, particularly the trans-isomer.

(f) CFCs can include, but are not limited to, R-11, R-12, R-13, R-113, R114, R115, and mixtures thereof.

(g) HCFCs can include, but are not limited to, R-123 (2,2-dichloro-1,1,1-trifluoroethane), R-124, R-141b, R-142b, R-22 (chlorodifluoromethane), and mixtures thereof.

(h) HFEs can include, but are not limited to, CF3OCHF2, CHF2OCH2F3, CHF2OCHF2, HFEs of the formula Rf—O—Rh, where O is oxygen, Rf is a perfluoroalkyl group and Rh is a saturated, unsubstituted alkyl group, particularly C2F5OCH3, C4F9OC2H5, C4F9OCH3, C3F7OCH3, and mixtures thereof.

(i) trans-1,2-dichloroethylene (j) water (k) carbon dioxide (l) atmospheric gases including, but not limited to, nitrogen, oxygen, and mixtures thereof.

The compositions of the present invention may be prepared or created by any means known in the art, including, but not limited to, blending, inadvertent mixing, as co-products or impurities from production, due to contamination from equipment or vessels, components being separately charged to the same pieces of equipment, etc.

In an embodiment of the present invention the working fluid is carbon dioxide.

In a highly preferred embodiment of the present invention the working fluid is selected from trans-HCFO-1233zd, trans-HFO-1234ze, HFO-1234yf, HFC-245fa, and mixtures thereof.

Flammability is an important property for many applications where it is very important or essential for the composition to be non-flammable, including particularly refrigerant and heat transfer applications. There are various methods of measuring the flammability of compounds and compositions, such as by measuring flash point or by ASTM E 681-01 as specified by ASHRAE Addendum 34p-92, as applicable. Preferably, the non-flammable compositions are non-flammable at ambient temperature and lower, preferably are non-flammable at 60° C. and lower, and even more preferably are non-flammable at 100° C. and lower. A greater range for non-flammability is beneficial by providing a greater degree of safety during use, handling, or transport.

The working fluid of the present invention preferrably has low toxicity, and more preferably is non-toxic. The working fluid of the present invention preferrably has moderate to low vapor pressure; preferably a vapor pressure of less than 70 bar at 25° C., even more preferably with a vapor pressure of less than 20 bar at 25° C.

The compositions of the present invention may include a stabilizer or stabilizers selected from free radical scavengers, acid scavengers, oxygen scavengers, polymerization inhibitors, corrosion inhibitors and combinations thereof. The preferred stabilizers of the present invention have minimal impact on the degradation of the hydrofluoroolefins and/or hydrochlorofluoroolefins when released into the atmosphere. Exemplary stabilizers include but are not limited to: 1,2-epoxybutane; glycidyl methyl ether; d,l-limonene; d,l-limonene oxide; 1,2-epoxy-2-methylpropane; nitromethane; diethylhydroxylamine; alpha-methylstyrene; isoprene; p-methoxyphenol; 3-mehoxyphenol; hydrazines; 2,6-di-t-butylphenol and hydroquinone The working compositions of the present invention are adsorbent working compositions comprising a metal-organic-framework and a working fluid.

The present invention is directed towards methods for storing, and optionally transporting, a working fluid by adsorbing the working fluid to a metal-organic-framework, providing an adsorbent working composition. The stored working fluid could then be released or removed from storage by heating and/or reducing the pressure of sorbent or adsorbent working composition.

The present invention is directed towards methods of separating mixed gases and/or liquids comprising the working fluids of the present invention. The method of separating mixtures of gases and/or liquids may be a batch process, continuous process, or combinations thereof. An embodiment of the present invention is a method of separating a mixture of gases and/or liquids including a working fluid comprising contacting a mixture of gases and/or liquids including a working fluid with a metal organic framework whereby the concentration of the working fluid in the mixture of gases and/or liquids is reduced via adsorption of the working fluid to the metal organic framework. An embodiment of the present invention is a method of storing a working fluid comprising contacting a metal organic framework with a working fluid whereby said working fluid is adsorbed by said metal organic frame work forming an adsorbent working composition.

In the present invention, the sorption of a working fluid, or component of a working fluid, to the MOF may occur at reduced temperature and/or elevated pressure. In an embodiment of the present invention, sorption of a working fluid, or component of a working fluid, to the MOF occurs at a relative pressure of P/Po greater than 0.0; in another embodiment greater than 0.01; in another embodiment greater than 0.05; in another embodiment greater than 0.1; in another embodiment greater than 0.2; in another embodiment greater than 0.3; in another embodiment greater than 0.4; in another embodiment greater than 0.5; in another embodiment greater than 0.6; in another embodiment greater than 0.7; in another embodiment greater than 0.8; in another embodiment greater than 0.9.

In the present invention, the desorption of a working fluid, or component of a working fluid, from the MOF may occur at elevated temperature and/or reduced pressure. In an embodiment of the present invention, desorption of a working fluid, or component of a working fluid, from the MOF occurs at a relative pressure of P/Po less than 1.0; in another embodiment greater than 0.9; in another embodiment greater than 0.8; in another embodiment greater than 0.7; in another embodiment greater than 0.6; in another embodiment greater than 0.5; in another embodiment greater than 0.4; in another embodiment greater than 0.3; in another embodiment greater than 0.2; in another embodiment greater than 0.1; in another embodiment greater than 0.05; in another embodiment greater than 0.02; in another embodiment greater than 0.01; in another embodiment approximately 0.

A preferred embodiment of the present invention is a process for separating mixtures of gases and/or liquids comprising a fluorinated working fluid where the MOF is NiDOBDC.

The present invention may further comprise, an additional sorbent used either together with the MOF or separately. Examples of additional sorbents include, but are not limited to, silica gel, activated carbon, zeolites, desiccants, and mixtures thereof.

In an embodiment of the present invention, the adsorbent working combination comprises working fluid of the present invention and a metal organic framework or covalent organic framework of the present invention. In a preferred embodiment of the present invention, the adsorbent working combination comprises from about 10 to about 1000 kg of working fluid to m³ of metal organic framework or covalent organic framework.

In an embodiment of the present invention, the adsorbent working combination can achieve an uptake of working fluid greater than about 10 wt %, preferably greater than about 20 wt %, more preferably greater than about 50 wt %, more preferably greater than about 100 wt %, more preferably greater than about 150 wt %.

EXAMPLES

Example 1

CuBTC and MDOBDC were synthesized and then water adsorption measurements were performed using an intelligent gravimetric gas analyzer (IGA). The mass uptake was measured as a function of pressure and the approach to equilibrium was monitored in real time. After equilibrium was established, the vapor pressure was increased to the next set pressure value, and the subsequent uptake was measured until equilibrium was reestablished. The increase in weight due to adsorption for each pressure step was plotted against the pressure. The adsorption of water in CuBTC was found to be 50 wt % at P/Po=0.3 or 10 mbar of pressure with very little desorption hysteresis. These results suggest that water loaded in CuBTC can be desorbed under a partial vacuum with very little additional heat input.

Using the method described above, water adsorption measurements were performed on MgDOBDC, NiDOBDC and CoDOBDC separately at room temperature. At P/P0=0.4, the water uptake in these three MOFs was found to be 24 wt % (NiDOBDC), 45 wt % (CoDOBDC) and 10 wt % (MgDOBDC). The water uptake in MgDOBDC approaches 60 wt % at P/Po=1. The results are summarized in FIGS. 6a, 6b, 6c and 6d.

Example 2

Water adsorption experiments were performed on MIL-101(Cr), MIL-100(Fe), and CoCo. The sorption of water in MIL-100Fe was found to be 80 wt % at P/P$_0$=0.9 with reversible adsorption and desorption of water molecules. The MIL-100Fe has pore diameters of 25 and 29 Å as confirmed by the single crystal X-ray diffraction. The MIL-101Cr was found to have mesoporous cage diameters of 29 and 34 Å. Water sorption of MIL-100(Fe) and MIL-101(Cr) indicate an uptake of 80 to 150 wt % at P/P$_0$=0.9. The LZnPyCl showed a water update of 12 wt % at P/P$_0$=0.95. Water sorption tests on CoCo indicate an uptake of water of 20 wt %. The results are summarized in FIGS. 7a, 7b, 7c and 7d.

Example 3

Figure 8:
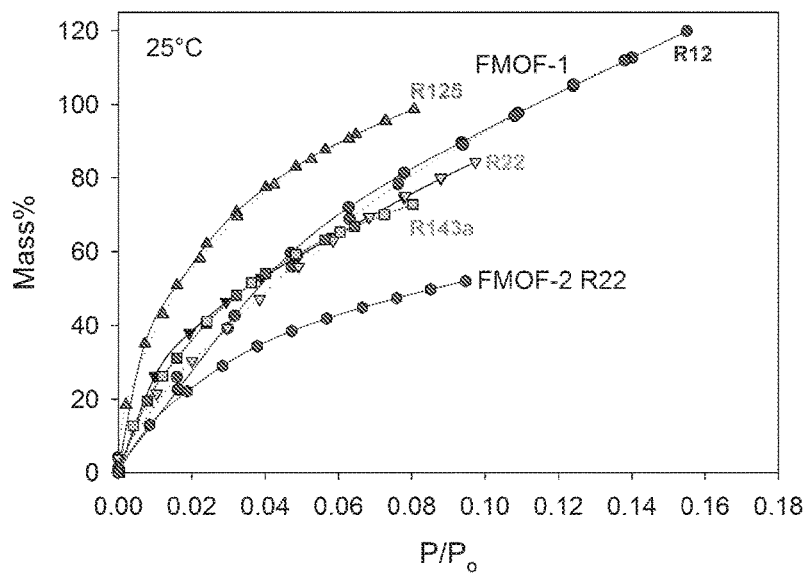
FIG. 8 is a graph of adsorption of R-12, R-22, R-143a, and R-125 in mass % versus P/Po.

Sorption experiments were conducted on MIL-101(Cr) (FMOF-1) with R-12 (dichlorodifluoromethane), R-125 (pentafluoroethane), R-143a (1,1,1-trifluoroethane), and R-22 (chlorodifluoromethane). Sorption experiments were conducted on MIL-100(Fe) (FMOF-2) with R-22 (chlorodifluoromethane). Results are summarized in FIG. 8.

Example 4

Figure 9:
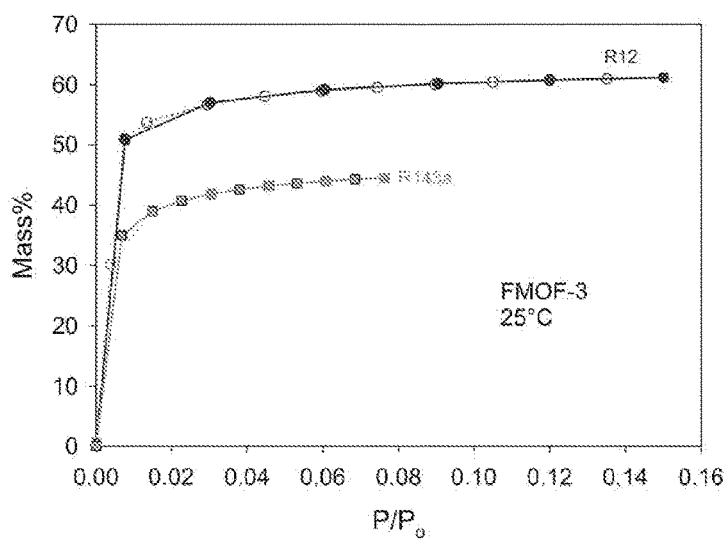
FIG. 9 is a graph of adsorption of R-12, and R-143a in mass % versus P/Po.

Sorption experiments were conducted on NiDOBDC (FMOF-3) with R-12 (dichlorodifluoromethane) and R-143a (1,1,1-trifluoroethane). Results are summarized in FIG. 9.

Example 5

Figure 10:
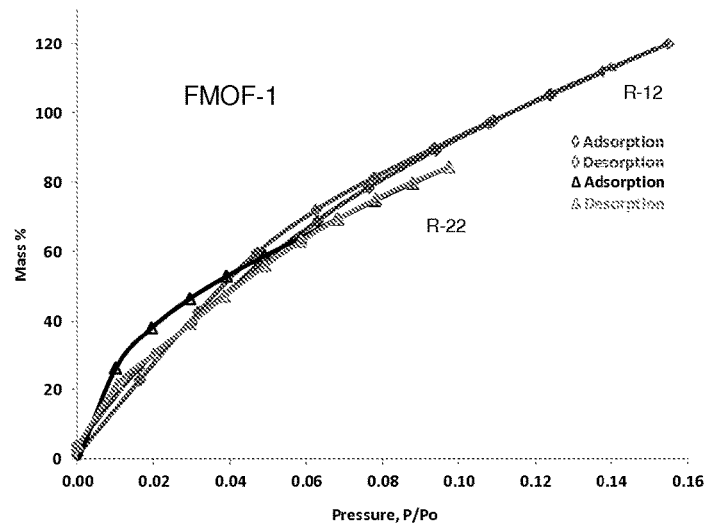
FIG. 10 is a graph of adsorption of R-12 and R-22 in mass % versus P/Po.

Sorption/desorption tests were performed on MIL-101 (Cr) (FMOF-1) with R-12 and R-22. Results are summarized in FIG. 10.

Comparative Example 6

The theoretical COP of an adsorption cycle can be approximated by the ratio of the heat of vaporization ($\Delta Hv$) and the heat of adsorption ($\Delta Ha$). The theoretical COP (Coefficient of Performance) for several known adsorbent/refrigerant pairs are listed in Table 1. The COPs are <1.0.

TABLE 1

Common Adsorbent/Refrigerant Pair Thermodynamic Properties

| Sorbent | Refrigerant | $\approx \Delta H_v$, J/g | $\approx \Delta H_a$, J/g | $COP_{theoretical}$ |
|---|---|---|---|---|
| Activated Carbon | Methanol | 1100 | 1900 | 0.6 |
| Activated Carbon | Ammonia | 1350 | 1900 | 0.7 |
| Activated Carbon | R134a | 217 | 393 | 0.5 |
| Silica Gel | Water | 2240 | 2500 | 0.9 |
| Zeolite | Water | 2240 | 3300 | 0.7 |

Example 7

The theoretical COP of pairs of carbon dioxide, butane, and R-134a with two MOFs, DHTP-Ni and Cu-BTC, are shown in Table 2. COPs greater than 2.0 are achievable.

TABLE 2

Mass Loading of Selected Refrigerants and $\Delta H_a$ Measured at 1 Bar and Room Temperature on Several Candidate MOHCs Used to Estimate COP for an Adsorption Chiller

| MOHC | Refrigerant | Refrigerant Uptake (wt %) | Heat of Adsorption (J/g) | $COP_{theoretical}$ |
|---|---|---|---|---|
| DHTP-Ni | $CO_2$ | 25 | 180 | 2.0[a] |
|  | $C_4H_{10}$ | 36 | 123 | 3.0 |
|  | R134a | 23 | 149 | 2.5 |
| Cu-BTC | $CO_2$ | 12 | 156 | 2.3[a] |
|  | $C_4H_{10}$ | 50 | 170 | 2.2 |
|  | R134a | 26 | 163 | 1.3 |

[a]Evaluated at 5 bar

Example 8

A comparison of the COP and bed size (volume-% relative to Silica-gel) for adsorption chillers operating at typical conditions using water as the refrigerant and with different sorbents is shown in Table 3.

TABLE 3

|  | Silica-Gel | HMOF-1 | HMOF-2 | HMOF-3 |
|---|---|---|---|---|
| COP | .49 | .72 | .75 | .86 |
| Bed Volume | 100% | 81% | 56% | 30% |

Example 9

Figure 11:
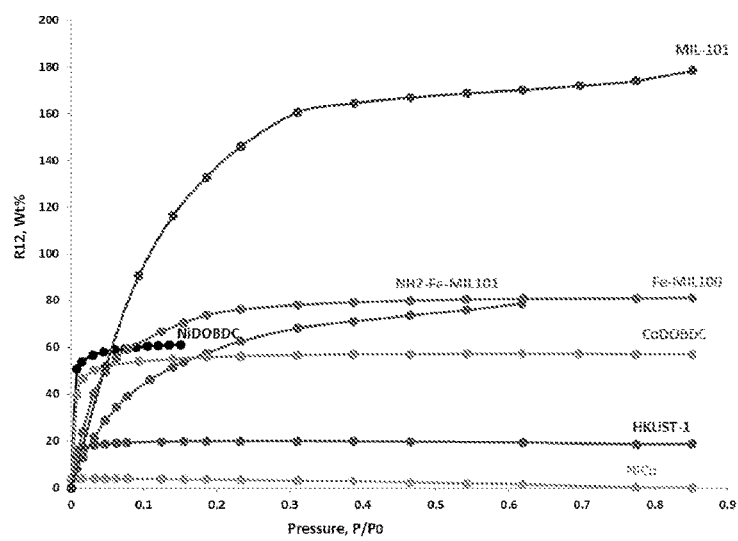
FIG. 11 is a graph of adsorption of R-12 in mass % versus P/Po.

Sorption experiments were conducted on MIL-101, NH2-Fe-MIL101, Fe-MIL100, NiDOBDC, CoDOBDC, HKUST-1, and NiCO with R-12 (dichlorodifluoromethane). Results are summarized in FIG. 11.

Example 10

Figure 12:
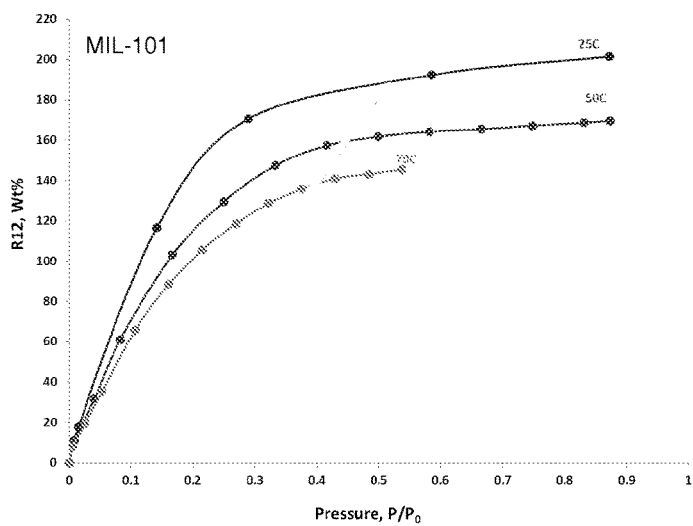
FIG. 12 is a graph of adsorption of R-12 in mass % versus P/Po.

Sorption experiments were conducted on MIL-101 with R-12 (dichlorodifluoromethane) at 25° C., 50° C., and 70° C. Results are summarized in FIG. 12.

Example 11

Sorption experiments were conducted on MIL-101 with R-12 (dichlorodifluoromethane) at 25° C., 50° C., and 70° C. Results are summarized in FIG. 12.

Example 12

Figure 13:
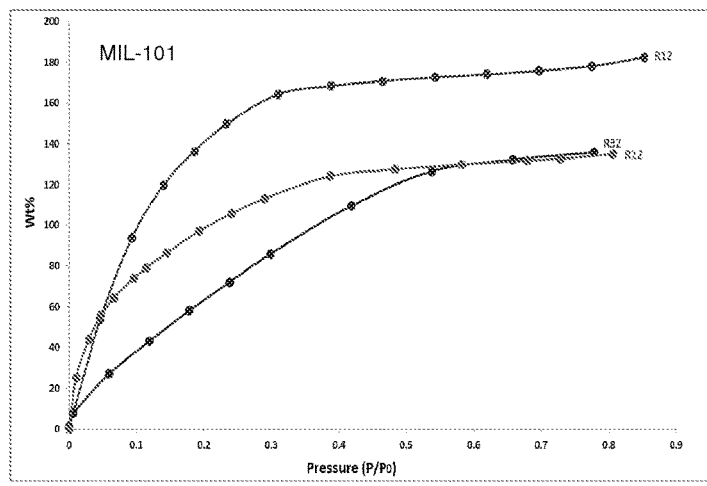
FIG. 13 is a graph of adsorption of R-12, R-22, and R-32 in mass % versus P/Po.
Figure 14:
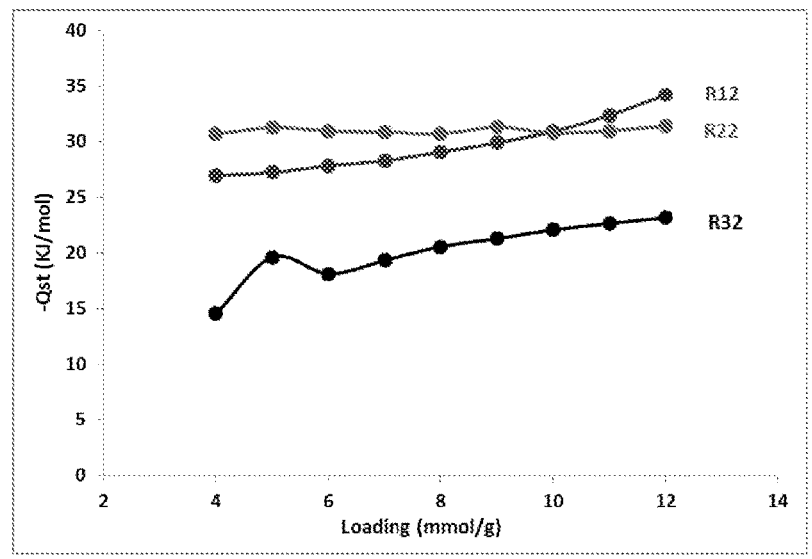
FIG. 14 is a graph of isoteric heats of R-12, R-22, and R-32 in KJ/mol versus mmol/g.

Sorption experiments were conducted at 25° C., 40° C., and 60° C. on MIL-101 with R-12 (dichlorodifluoromethane), R-22 (chlorodifluoromethane), and R-32 (difluoromethane). Results are summarized in FIG. 13 and isoteric heats are shown in FIG. 14.

Example 13

Figure 15:
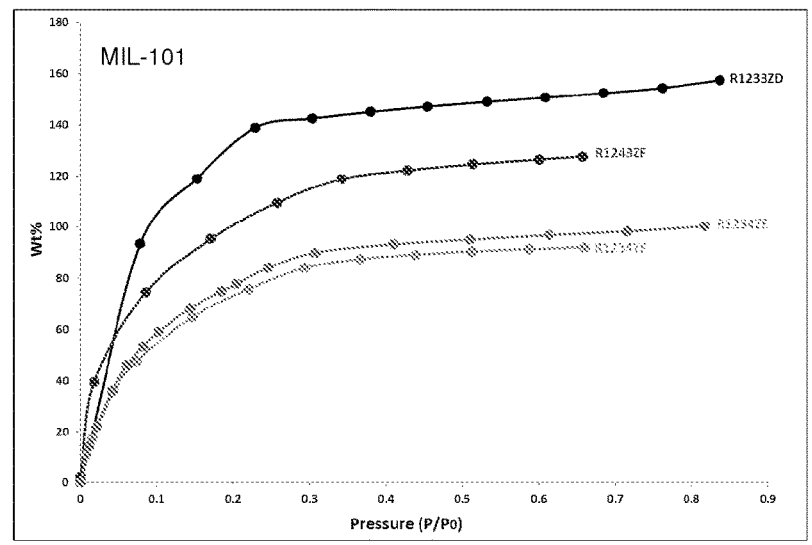
FIG. 15 is a graph of adsorption of R-1233zd, R-1243zf, 1234ze, and 1234yf in wt % versus P/Po.
Figure 16:
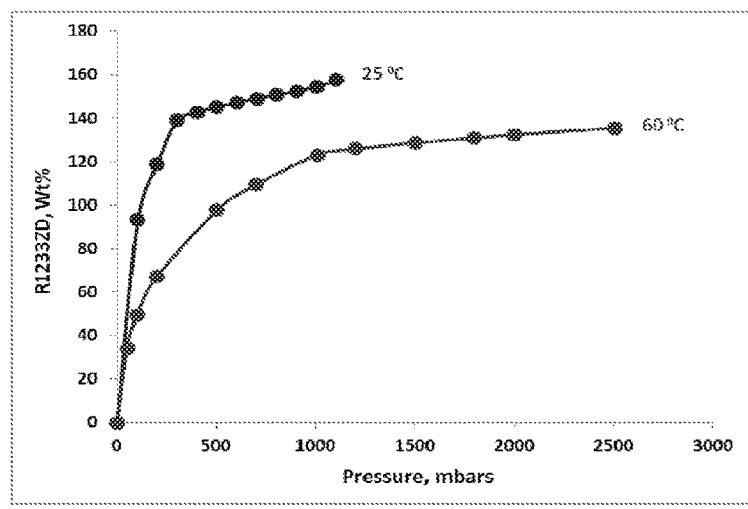
FIG. 16 is a graph of adsorption of R-1233zd in wt % versus mbar.
Figure 17:
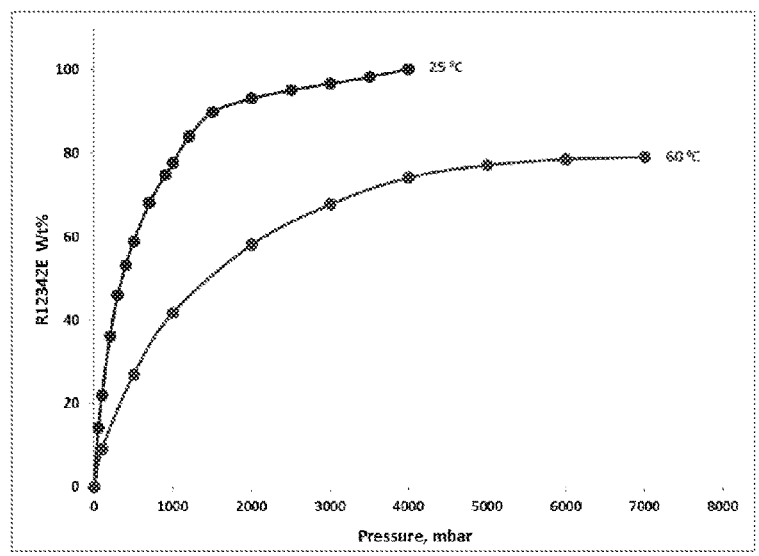
FIG. 17 is a graph of adsorption of R-1234ze in wt % versus mbar.
Figure 18:
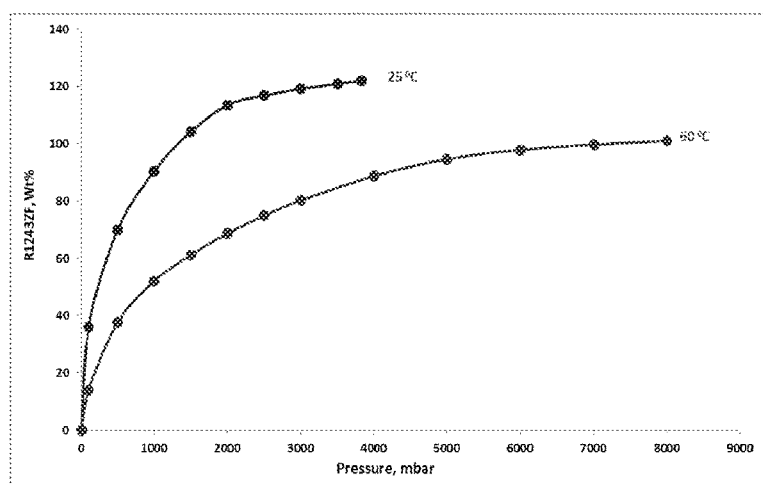
FIG. 18 is a graph of adsorption of R-1243zf in wt % versus mbar.
Figure 19:
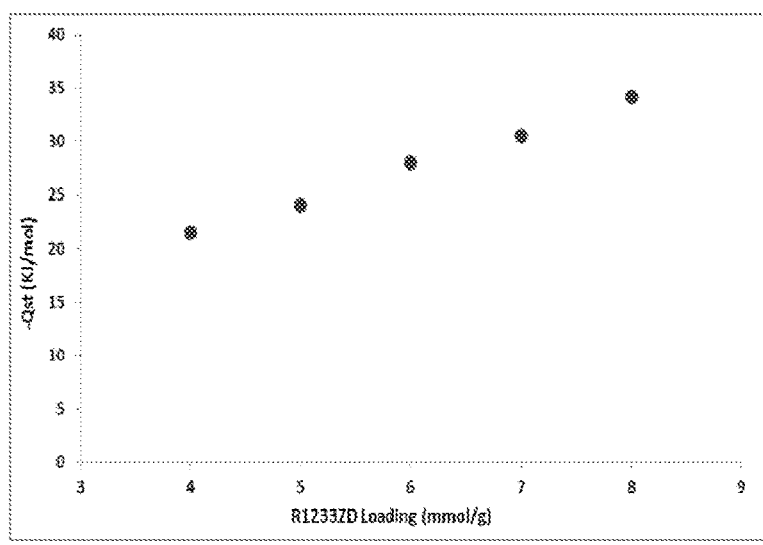
FIG. 19 is a graph of isoteric heats of R-1233zd in KJ/mol versus mmol/g.
Figure 20:
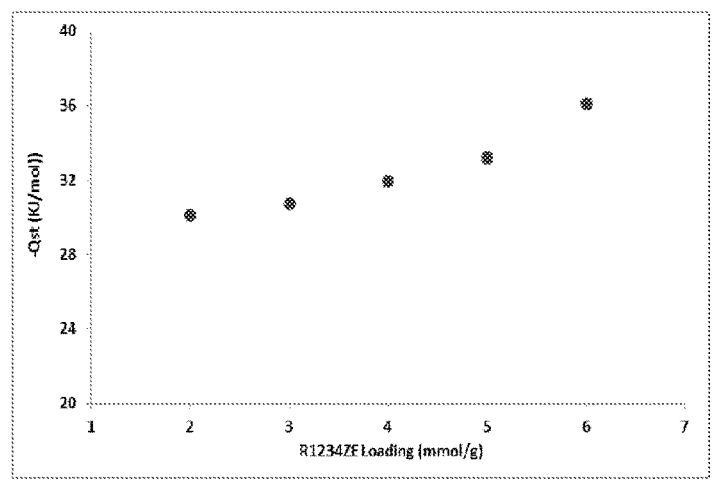
FIG. 20 is a graph of isoteric heats of R-1234ze in KJ/mol versus mmol/g.
Figure 21:
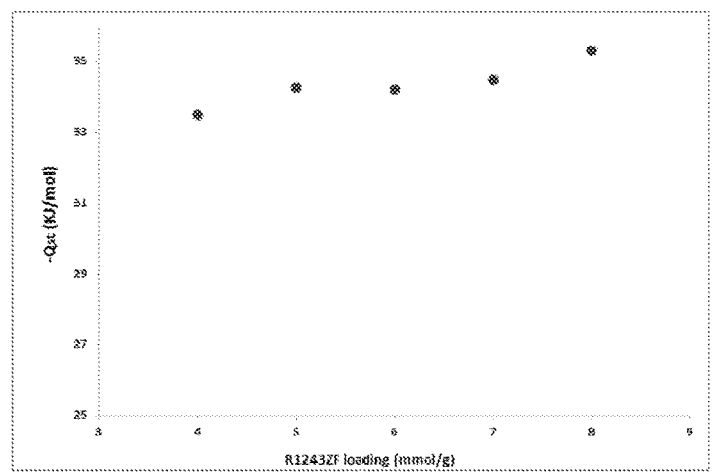
FIG. 21 is a graph of isoteric heats of R-1243zf in KJ/mol versus mmol/g.

Sorption experiments were conducted at 25° C. and 60° C. on MIL-101 with R1233ZD (trans-1-chloro-3,3,3-trifluoropropene), R1234ZE (trans-1,3,3,3-tetrafluoropropene), R1234YF (2,3,3,3-tetrafluoropropene), and R1243zf (3,3,3-trifluoropropene). Sorption results are shown in FIG. 15; sorption results for R1233ZD, R1234ZE, and R1243ZF are shown in FIGS. 16, 17, and 18 respectively; isoteric heats of R1233ZD, R1234ZE, and R1243ZF are shown in FIGS. 19, 20, and 21 respectively.

Example 14

Figure 22:
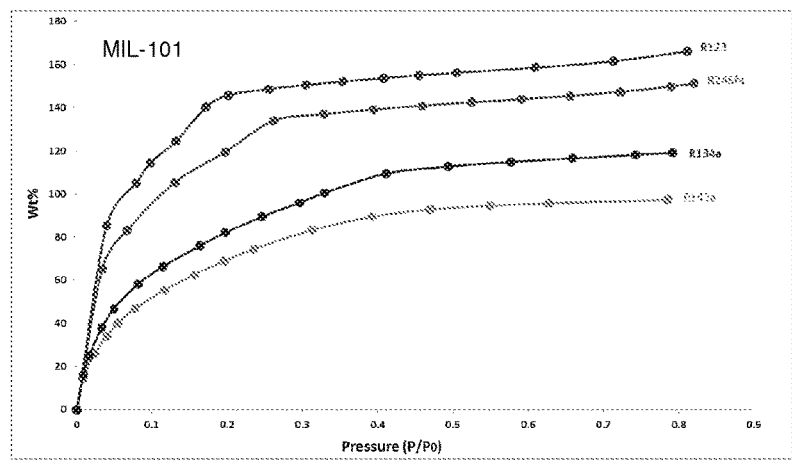
FIG. 22 is a graph of adsorption of R-123, R-245fa, R-134a, and R-143a in wt % versus P/Po.

Sorption experiments were conducted at 25° C. on MIL-101 with R123 (2,2-dichloro 1,1,1-trifluoroethane), R245fa (HFC-245fa; 1,1,1,3,3-pentafluoropropane), R134a (HFC-134a; 1,1,1,2-tetrafluoroethane), and R143a (HFC-143a; 1,1,1-trifluoroethane). Results are summarized in FIG. 22.

Example 15

Figure 23:
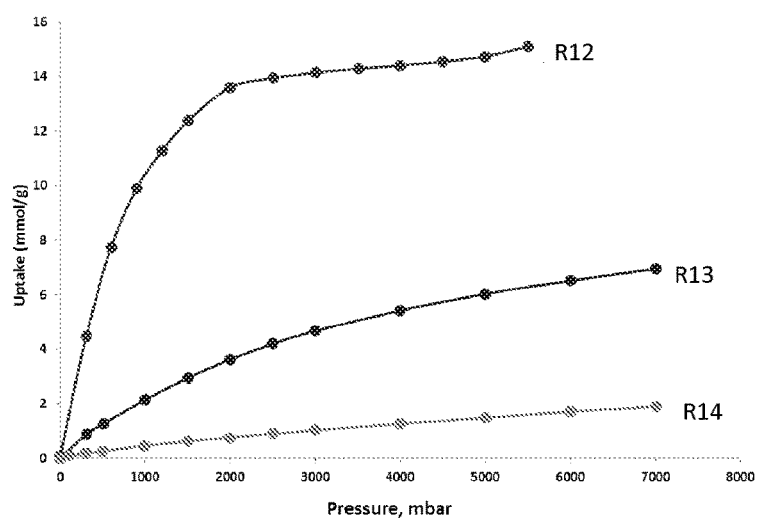
FIG. 23 is a graph of adsorption of R-12, R-13, and R-14 in mmol/g versus mbar.

Sorption experiments were conducted at 25° C. on MIL-101 with R12 (dichlorodifluoromethane), R13 (chlorotrifluoromethane), and R14 (tetrafluoromethane). Results are summarized in FIG. 23.

Example 16

Figure 24:
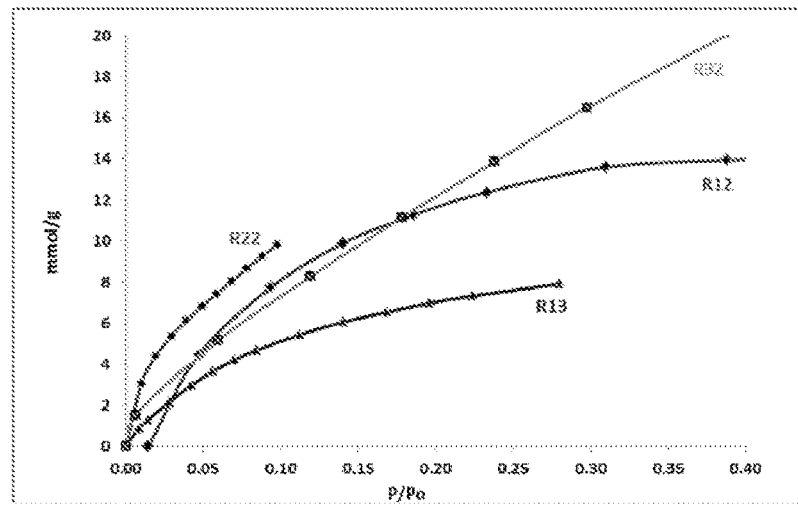
FIG. 24 is a graph of adsorption of R-12, R-13, R-22, and R-32 in mmol/g versus P/Po.

Sorption experiments were conducted at 25° C. on MIL-101 with R12 (dichlorodifluoromethane), R13 (chlorotrifluoromethane), R22 (chlorodifluoromethane), and R32 (difluoromethane). Results are summarized in FIG. 24.

Example 17

Figure 25:
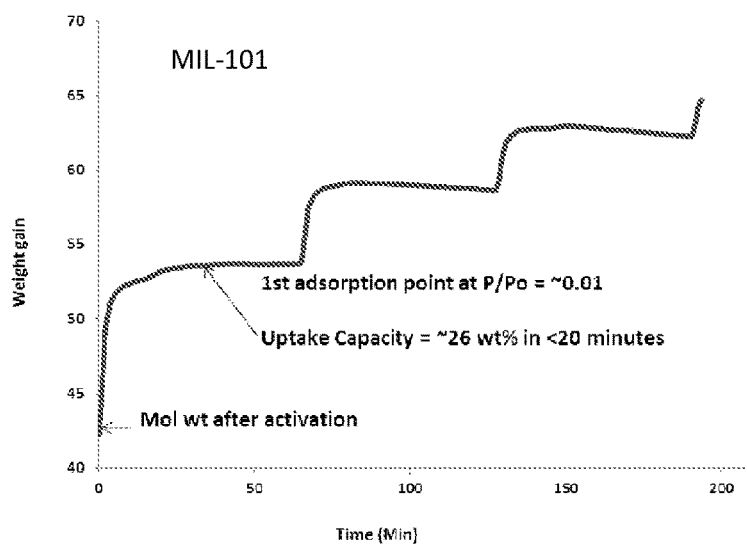
FIG. 25 is a graph of sorption kinetics of R-22 with MIL-101 in weight gain versus time in minutes.

Sorption kinetic experiments were conducted at 25° C. on MIL-101 with R22 (chlorodifluoromethane). Results are summarized in FIG. 25.

Example 18

Sorption experiments were conducted at 25° C. on with R-12 on MOF-74(Fe), MOF-74(Ni), and MOF-74(Co). Results with MOF-74(Ni) showed high uptake at low P/Po.

Example 19

An adsorption chiller is operated using trans-HCFO-1233zd as the refrigerant and MIL-101 as the sorbent to provide chilled water at about 50° F. The COP is above 0.6.

Example 20

An adsorption chiller is operated using trans-HFO-1234ze as the refrigerant and MIL-101 as the sorbent to provide chilled water at about 50° F. The COP is above 0.6.

Example 21

An adsorption chiller is operated using trans-HFO-1234yf as the refrigerant and MIL-101 as the sorbent to provide chilled water at about 50° F. The COP is above 0.6.

Example 22

An adsorption chiller is operated using HFC-245fa as the refrigerant and MIL-101 as the sorbent to provide chilled water at about 50° F. The COP is above 0.6.

Example 23

Figure 26:
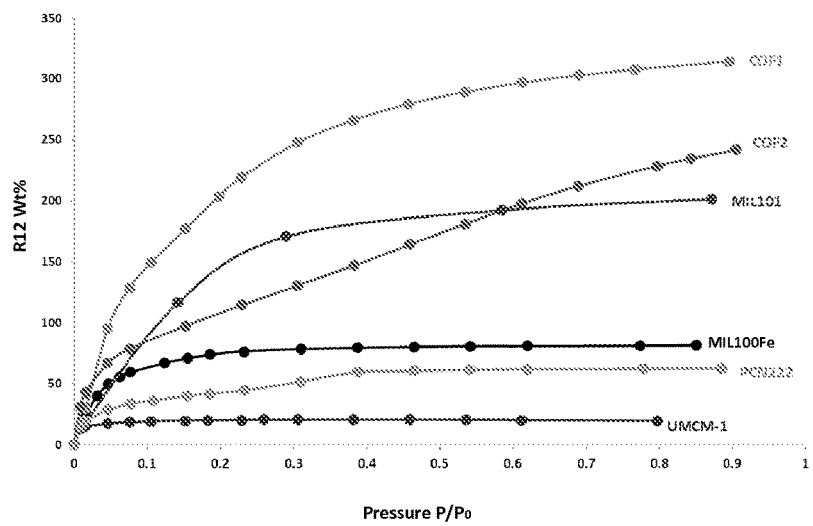
FIG. 26 is a graph of adsorption of R-12 in wt % versus P/Po.
Figure 27:
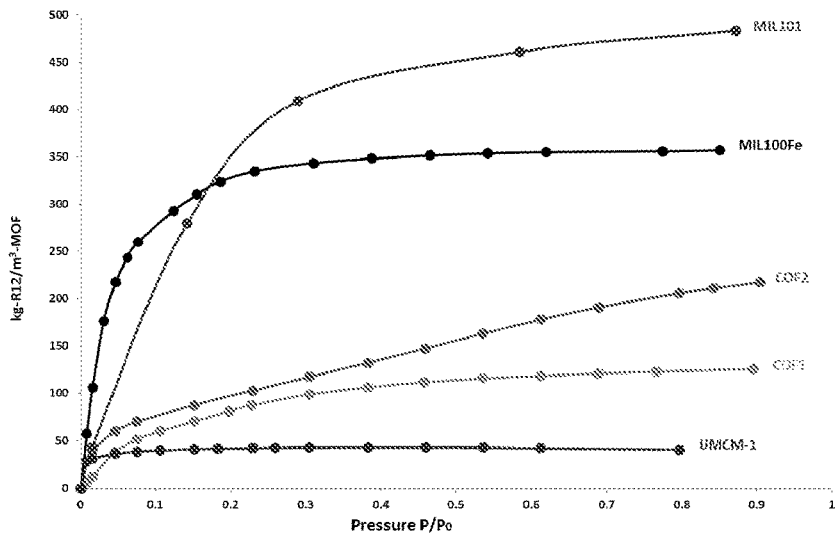
FIG. 27 is a graph of adsorption of R-12 in (kg-R12/$M^3$-MOF) versus P/Po.

Sorption experiments were conducted on with R-12 on covalent organic framework COF-1, covalent organic framework COF-2, UMCM-1, PCN222, MIL-100 (MIL100Fe), and MIL-101 (MIL100). Results are shown in FIG. 26 and FIG. 27.

The invention claimed is:

1. An adsorbent combination comprising a metal-organic-framework selected from the group consisting of CuBTC, MDODBC, FMOF-2CU, MIL-101(Cr), MIL-100(Fe), CoCo, ZnCo, and LZnPYCl where M is selected from the group consisting of Mg, Ni, Zn, or Co and a working fluid selected from the group consisting of HFO, HCFO, and mixtures thereof.

2. An adsorption chiller system comprising the adsorbent combination of claim 1.

3. An adsorption chiller system comprising the adsorbent combination of claim 1 in combination with a refrigerant compressor or expander components.

4. An adsorption chiller system comprising more than one adsorbent combination of claim 1 arranged in a parallel or series configuration.

5. An adsorption chiller system comprising at least one adsorbent combination of claim 1 in a heat engine configuration.

6. The adsorption chiller system of claim 5 wherein said heat engine configuration comprises at least one microchannel heat exchanger.

7. An adsorption chiller system of claim 4 designed to produce output temperature suitable for but not limited to refrigeration, freezing, and cryogenic cooling.

8. The adsorbent combination of claim 1 wherein the HFO is selected from the group consisting of pentafluoropropenes (HFO1225), tetrafluoropropenes (HFO1234), trifluoropropenes (HFO1243), all tetrafluorobutene isomers (HFO1354), all pentafluorobutene isomers (HFO345), all hexafluorobutene isomers (HFO336), all heptafluorobutene isomers (HFO1327), all heptafluoropentene isomers (HFO1447), all octafluoropentene isomers (HFO1438), all nonafluoropentene isomers (HFO1429), and mixtures thereof).

9. The adsorbent combination of claim 1 wherein the HFO is selected from the group consisting of trans-1,3,3,3-tetrafluoropropene (trans-HFO-1234ze); 2,3,3,3-tetrafluoropropene (HFO-1234yf), (cis and/or trans)-1,1,1,3,3,3-hexafluorobutene (HFO-1336mzz), and mixtures thereof.

10. The adsorbent combination of claim 1 wherein the HCFO is a chlorotrifluoropropene.

11. The adsorbent working combination of claim 1 wherein the HCFO is trans-1-chloro-3,3,3-trifluoropropene (trans-HCFO-1233zd).

* * * * *

UNITED STATES PATENT AND TRADEMARK OFFICE
CERTIFICATE OF CORRECTION

PATENT NO. : 10,266,737 B2
APPLICATION NO. : 14/420042
DATED : April 23, 2019
INVENTOR(S) : Van Horn et al.

Page 1 of 1

It is certified that error appears in the above-identified patent and that said Letters Patent is hereby corrected as shown below:

In the Specification

Column 1, Line 10 insert:
--STATEMENT OF GOVERNMENT RIGHTS
This invention was made under CRADA PNNL/319 between Power Partners, Inc., Arkema Inc., and Battelle Memorial Institute, as operator of the Pacific Northwest National Laboratory on behalf of the United States Department of Energy. The Government has certain rights in this invention.--

Signed and Sealed this
Fourteenth Day of July, 2020

Andrei Iancu
*Director of the United States Patent and Trademark Office*